United States Patent [19]

MacLennan

[11] Patent Number: 5,585,476
[45] Date of Patent: Dec. 17, 1996

[54] MOLECULAR CLONING AND EXPRESSION OF G-PROTEIN COUPLED RECEPTORS

[76] Inventor: Alexander J. MacLennan, 7811 NW. 35th Pl., Gainesville, Fla. 32606

[21] Appl. No.: 196,989

[22] Filed: Feb. 15, 1994

[51] Int. Cl.$^6$ .......................... C07K 14/705; C12N 15/12
[52] U.S. Cl. .................. 536/23.5; 435/691; 435/252.3; 435/320.1; 530/350
[58] Field of Search ................................ 435/69.1, 252.3, 435/320.1; 530/350; 536/23.5

[56] References Cited

PUBLICATIONS

Biochem. Biophys. Rec. Conn. 190:1104–1109, 15 Feb. 1993, Okazaki, Molecular Cloning of a Novel Putative G Protein Coupled Receptor Expressed in the Cardiovascular System Yarden, Y. A. Ullrich (1988) "Growth Factor Receptor Tyrosine Kinases" Ann. Rev. Biochem. 57:443–478.

Devreotes, P. (1989) "*Dictyostelium discoideum*: A Model System for Cell–Cell Interactions in Development" Science 245:1054–1058.

Hanley, M. R. (1989) "Mitogenic neurotransmitters" Nature 340:97.

Zachary, I., P. J. Woll, E. Rozengurt (1987) "A Role for Neuropeptides in the Control of Cell Proliferation" Dev. Biol. 124:295∝308.

Young, D., G. Waitches, C. Birchmeier, O. Fasano, M. Wigler (1986) "Isolation and Characterizatin of a New Cellular Oncogene Encoding a Protein with Multiple Potential Transmembrane Domains" Cell 45:711–719.

Gutkind, J. S., E. A. Novotny, M. R. Brann, K. C. Robbins (1991) "Muscarinic acetylcholine receptor subtypes as agonist–dependent oncogenes" Proc. Natl. Acad. Sci. USA 88:4703–4707.

Julius, D., T. J. Livelli, T. M. Jessell, R. Axel (1989) "Ectopic Expression of the Serotonin 1c Receptor and the Triggering of Malignant Transformation" Science 244:1057–1062.

Julius, D., K. N. Huang, T. J. Livelli, R. Axel, T. M. Jesell (1990) "The 5HT2 receptor defines a family of structurally distinct but functionally conserved serotonin receptors" Proc. Natl. Acad. Sci. USA 87:928–932.

MacLennan, A. J., G. D. Frantz, R. C. Weatherwax, N. J. K. Tillakaratne, A. J. Tobin (1990) "Expression of mRNAs That Encode D2 Dopamine Receptor Subtypes: Anatomical, Developmental, and Pharmacological Studies" Molec. Cell. Neurosci. 1:151–160.

Loh, E. Y., J. F. Elliott, S. Cwirla, L. L. Lanier, M. M. Davis (1989) "Polymerase Chain REaction with Single–Sided Specificity: Analysis of T Cell Receptor δ Chain" Science 243:217–220.

Sanger, F., S. Nicklen, A. R. Coulson (1977) "DNA sequencing with chain–terminating inhibitors" Proc. Natl. Acad. Sci. USA 74:5463–5467.

Chirgwin, J. M., E. Przbyla, R. J. MacDonald, W. J. Rutter (1979) "Isolation of biologically Active Ribonucleic Acid from Sources Enriched in Ribonuclease" Biochem. 18:5294–5299.

*Primary Examiner*—John Ulm
*Attorney, Agent, or Firm*—Saliwanchik & Saliwanchik

[57] ABSTRACT

The cloning and expression of two novel rat cDNAs "H218" and "rat-edg") which encode two members ("$p^{H218}$" and "$p^{rat-edg}$") of the G-protein coupled receptor superfamily of proteins is described. The amino acid sequence similarity between "$p^{H218}$" and "$p^{rat-edg}$" suggests that they may be activated by the same endogenous ligand(s). The expression pattern of mRNA transcripts of both genes in cell lines, various rat tissues and developing rat brain suggests that they both play a role in cell proliferation and/or differentiation. The polynucleotide molecules, proteins, and antibodies of the subject invention can be used in both diagnostic and therapeutic applications.

2 Claims, 12 Drawing Sheets

```
-155  CCCCCCCCCCCCTCGAGCACAGCCAACAGTCAGCCAAGTCAGCCACTGGCTGTCCCGG
 -95  GGCGCAGAGCCAAGGCCACTCAGGCCAGGCAGCCTGCCCGGCCCTAGCCAGTGCT
 -35  CAGTCCCATGGCCCCGGCCCACTGAGCCCCACCATGGCCGGTTTATACTCAGAGTAC    8
                                        MetGlyLeuTyrSerGluTyr

25  CTCAATCCTGAGAAGTTCAGGAACACTACAATTACACCAAGGAGACGCTGGACATGCAG   28
      LeuAsnProGluLysPheArgAsnThrThrIleHisGlnGluThrLeuAspMetGln

85  GAGACGCCCTCCGCAAGGTGGCCCTCCGCCTTCATCATCATTTATGTGTGCCATCGTG   48
      GluThrProSerArgLysValAlaLeuArgLeuHisHisHisLeuCysValIleVal

145  GTGGAGAACCTTCTGGTGCTAATCGCAGTGGCCAGGAACAGCAAGTTCCACTCAGCCATG   68
      ValGluAsnLeuLeuValLeuIleAlaValAlaArgAsnSerLysPheHisSerAlaMet

205  TACCTGTTCCTCGGCAACCTGGCAGCCCTGCTGGCCAGGCCGTGGCCCTTCGTGGCC   88
      TyrLeuPheLeuGlyAsnLeuAlaAlaSerAspLeuLeuAlaGlyValAlaPheValAla

265  AACACCCTTGCTCTCCGGACCTGTCACCCTGTCCTAACTCCCTTGCAGTGGTTTGCCGA  108
      AsnThrLeuLeuSerGlyProValThrLeuThrProLeuGlnTrpPheAlaArg

325  GAGGGTTCAGCCTTCATCACGCCTCTCTGCCTCTTCAGCCTCCTGGCCATTGCCATC   128
      GluGlySerAlaPheIleThrLeuLeuSerAlaSerValPheSerLeuLeuAlaIleAlaIle

385  GAGAGACAAGTGGCCATCGCAAGGCTCAAGGTGGTCCTGCCAGTGACAAAAGCTGTGAATG  148
      GluArgGlnValAlaIleAlaLysValLeuLysLeuTyrGlySerAspLysSerCysArgMet

445  TTGATGCTCATTGGGCCCTCTTGGCTGATATCGCCCTGATTCTGGGGCCTTGCCCATCCTG  168
      LeuMetLeuIleGlyAlaSerTrpLeuIleSerLeuIleLeuGlyLeuProIleLeu

505  GGCTGGAATTGTCTGGACCATCTGGAGGCTTGCTCCACTGCTGCCCCCCTCTATGCTAAG  188
      GlyTrpAsnCysLeuAspHisLeuGluAlaCysSerThrValLeuProLeuTyrAlaLys

565  CACTATGTGCTCTGCGTGGTCACCATCTTCTCTGTCATCTTACTGGCTATCGTGGCCTTG  208
      HisTyrValLeuCysValValThrIlePheSerValIleLeuLeuAlaIleValAlaLeu
```

FIG. 1A

```
625   TACGTCCGAATCTACTTCGTAGTCCGCTCAAGCCATGCGGACGTTGCTGTCCTCAGACG     228
      TyrValArgIleTyrPheValValArgSerHisAlaAspValAlaGlyProGlnThr

685   CTGGCCCTGCTCAAGACAGTCACCATCGTACTGGGTGTTTCATCATCTGCTGGCTGCCG     248
      LeuAlaLeuLeuLysThrValThrIleValLeuGlyValPheIleIleCysTrpLeuPro

745   GCTTTTAGACATCCTCTCTTAGACTCTACCTGTCCCGGCCTGTCCTGTCCTCCTCTAC     268
      AlaPheSerIleLeuLeuLeuAspSerThrCysProValArgAlaCysProValLeuTyr

805   AAAGCCCATTATTCTTCTTGCCTTCGCCACCCTCAACTCTGCTCAACCCTGTATCTAT     288
      LysAlaHisTyrPhePheAlaThrLeuLeuAsnSerLeuLeuAsnProValIleTyr

865   ACATGGCGTAGCCGGGACCTTCGGAGGAGTACTGAGGCCCCTGCTGTGGCGGCAG     308
      ThrTrpArgSerArgAspLeuArgArgValLeuArgProLeuLeuCysTrpArgGln

925   GGGAAGGGAGCAACAGGGCGCAGAGTGGGAACCCTGGTCACCGACTCCTGCCCCTCCGC     328
      GlyLysGlyGlyAlaThrGlyArgArgGlyAsnProGlyHisArgLeuLeuProLeuArg

985   AGCTCCCAGCCCCTGGAGAGAGGCTTGCATATGCCTACATGCCAACATTCTGGAGGGC     348
      SerSerSerSerLeuGluArgGlyLeuHisMetProThrSerProThrPheLeuGluGly

1045  AACACAGTGGTCTGAGGGAAATGTGAACTGATCTGTAACCAAGCCACAGAGAGCTCT     352
      AspThrValVal
```

FIG. 1B

```
1105 GTGGGGAGAGACCAGGTGACCTCATCATGTCCCTCAGTGCCCACAGTCTCTGGAGGAACTGA
1165 CCACGGCTCATAGTCAGGTGCTCAGGTGCCAACGGAGGCACTGACTAATCAGATTGTAGTACTGTG
1225 ACTGTGGGACCATTAAGGTCTAGGGGTCGGACAGCAGGCTCGAGTTTAGGGCTAGACATTT
1285 GCCACTTGGTACATAGGGTGTCGGCATCGTGTCCTGTCCTATCTTCCAGCTTCCCGGTTCC
1345 CTTCCTGCCTCCCTCCTTTAAGGCCCTCTACATAGCCCGGCTGGCTAGAGCTTGCTG
1405 TGCAGACCAGCTGGACCTGACCTCCCAGAGATAGATCAACTAACTGTCCTGAGTGCT
1465 GGGATTTTAAAGCCGTGTGCCCCCACACACCCGCTCCTGCCACCTTCTCCCTGTCTCTG
1525 GGCCACTTGTGAGGAAACACTCTCCCCAGAGGACCCAAGCCTTCTTCCCTTCCTTCTGTG
1585 AGGCCTGAATCACACAGCTTGCTGCTTCTCCCTTTATCAACTGCTGCTTCTCCCTTTATGCTCAG
1545 TTCAGGGGAAACCACTGTGGGCAGGAGGGTCCTGGGATCCCAGTTTTTATGCTCAG
1605 ATCTCACTGAGCACTTGCTTTATTGGGAGCAGAGAGGAATCAGCTGAGGCAGTGTGGGG
1665 CAGATGTGAGGAGAATTTGGGCTTCCTCCTGTGAGAAAACTCTAGGGAGGCGTTGGTTAT
1725 TCCTGGAACCCAGCCTCTCTCCCCACGAACTCTCACACCGTCGCAGCCTTGAGCTGGATGC
1785 AAAGGCTGCTTTCAATTTGTCTTTGTAGTTTTGTTTTTGTTTTTGTTTTTTAAATT
1845 GGGACAGGATCTCACGTACCCCAGGCTGGCCTCCGACTCACTATGTAGCCAAGGCTGGCT
1905 TTTGGACTTCTGACCCCTCCCGCCTCCGCTTCTGGAGTGCAGGTATTACAAGGGTGTACCAC
1965 CACCACCACCACCAACAACAACAACCTGTCCTTGAAAACTATCATGA
2025 ATGACATGTTCACATAGCCTTGGGTGGCCAAGGACATCCCGGATACTCTTATGCATCT
2085 TCCTTGAAGGACTTTGCTAAATCCTGTGTGAGAGTAGAAATCCAATACGGTACAAACGG
2145 TATTTAGTGTGTCTGTGTATCAGTGTGGGTCTGTGACCTCTGACCTCCTATCCCAGTGTGGTGC
2205 TGTCTGTGACCTCTTATGTGCACATCCGTGTCAAGACTGCTAGAGACTGCTAGAGATGGACGGGGTGTG
2265 TGTGTTGTGGGGTCTGACCATGATCAGGCCCTGGGAATTGCTGAATCATCTCTCCC
2325 ACACACAGACACACACCTCCGCCTTAAAGAAATGTGAAAGAAAAGGCTGAGGAAGGGG
2385 AGATTTGGAGGCAAGGAGCCAGTGTCGGAGTGTCTCCCCATAAAGCTCCCAGATG
2445 TCCCCCTTGTGCTGAAACCCAGAACTGGGCAATAAACAGTTCAATTTCTCTTGAAAA
2505 AAA
```

```
                            ┌─TMD#6─┐
P^H218  LYV..RIYFVRSSHADVAGP.......QTLALLKVTIVLGVFIICWLPAFSILLDSTCPVRACPVLY
D2      LLVYIKIYIVLRKRRKRVNTK-(112)-KEKKATQMLAIVLGVFIICWLPFFITHILNIHC...DCNI.P
β2      LVVMFVYSRVFQVAKRQLQK-(33)--KEHKALKTLGIIMGIFTLCWLPFFIVNIVHVI...QDNLI.P
α2      LVVMFVYSRVFQVAKRQLQK-(138)-REKRFTFVLAVIGVFVVCWFPFFFTYTLTAV....GCSV.P
5HT1A   CLIMILVVVRIYQIAKRRTRV-(138)-REKRFTFVLAVIGVFVVCWFPFFFTYTLTAV....GCSV.P
M1      LILMLVLYGRIFRAARFRIPK-(111)-RERKTVKTLGIIMGTFILCWLPFFIVALVLPFCE.SSCHM.P
SK      VTVMCTLWRIYRETENRARE-(138)-KEKKAARTLSAILLAFIVTWTPYNIMVLVSTFC..KDC.V.P
        LVVMFVAYSVIGLTLWRRSVP-(13)--AKKKFVKTMVLVVTFAICWLPYHLYFILGTFQEDIYCHKFI

┌─TMD#7─┐
        KAHV..FFAFATLNSILNPVIYTWRSRDLRREVLRPIHC---(46)
        PVLYSAFTWLGYVNSAVNPIIYTTFNIEFRKAFMKILHC
        KEVYILLNWLGYVNSAFNPLIYC..RSPDFRIAFQELL..C---(37)
        RTLFKFFWFGYCNSSLNPVIYTIFNHDFRRAFKKIL..C---(8)
        TLLGAIINWLGYSNSLLNPVIYAYFNKDFQNAFKKIIKC---(5)
        ETLWELGYWLCYVNSTINPMCYALCNKAFRDTFRLLLLC---(25)
        QQVVLALFWLAMSSTMYNPIIYCCLNHRFRSGFRLAFRC---(63)
```

3.2 kb            H218

-260 TTTGCTGGTCTCCGTCAGTCGCCGACAGCAGCAAGATGCGGATCGCGCGGGTGTAG
-206 ACCCGGAGCCCGGCGGACGCCAGCTTGTCCCGCTTGAGCGAGGCTGCTGTTTCTCGAGG
-146 CCTCTCCAGCCAAGGAAAAACTACATAAAAAGCATCGGATTGCTTGCTGACCTGCCTT
-86 GCTGTAACTGAAGGCTCGCTCAACCTCGCCCTCTAGCGTTTGTCTGGAGAAGTACCACCC
-26 CGGGCTCCTGGGGACACAGTTGCGGCTATGGTGTCCTCCACCAGCATCCCAGTGGTTAAG
MetValSerSerThrSerIleProValValLys 11

34 GCTCTCCGCAGCCAAGTCTCCGACTATGGCAACTATGATATCATAGTCCGGCATTACAAC
AlaLeuArgSerGlnValSerAspTyrGlyAsnTyrAspIleIleValArgHisTyrAsn 31

94 TACACAGGCAAGCTGAACATCGGAGTGGAGAAGGACCATGGCATTAAACTGACTTCAGTG
TyrThrGlyLysLeuAsnIleGlyValGluLysAspHisGlyIleLysLeuThrSerVal 51

154 GTGTTCATTCTCATCCTGCTGCTTGATCATCCTAGAGAATATATTTGTCTTGCTAACTATT
ValPheIleLeuIleLeuCysCysLeuIleLeuIleLeuGluAsnIlePheValLeuThrIle 71

214 TGGAAAACCAAGAAGTTCCACCGGCCCATGTACTATTTCATAGGCAACCTAGCCCTCTCG
TrpLysThrLysLysPheHisArgProMetTyrTyrPheIleGlyAsnLeuAlaLeuSer 91

274 GACCTGTTAGCAGGAGTGGCTTACACAGCTAACCTGCTGTTGTCTGGGGCCACCACCTAC
AspLeuLeuAlaGlyValAlaTyrThrAlaAsnLeuLeuLeuSerGlyAlaThrThrTyr 111

334 AAGCTCACACCTGCCCAGTGGTTTCTGCGGGAAGAAGTATGTTTGTGGCTCTCTGCC
LysLeuThrProAlaGlnTrpPheLeuArgGluGlySerMetPheValAlaLeuSerAla 131

394 TCAGTCTTCAGCCTCCTTGCTATGCCATTGAGCGCTACATCACCATGCTGAAGATGAAA
SerValPheSerLeuLeuAlaLeuAlaIleGluArgTyrIleThrMetLeuLysMetLys 151

454 CTACACAACGGCAGCAACAGCTCGCGCTCCTTTCTGCTGATCAGTCGCCTGCTGGTCATC
LeuHisAsnGlySerAsnSerArgSerPheLeuLeuIleSerAlaCysTrpValIle 171

FIG. 7A

```
 514 TCCCTCATCCTCTGGGTGGGCTGCCTGGAACTGATCAGCTGCTGTCCAGC
     SerLeuIleLeuGlyGlyLeuProIleMetGlyTrpAsnCysIleSerSerLeuSerSer  191

594 TGCTCCACCGTGCTCCCGCTCTACCAAGCACTATATTCTCTTCTGCACCACCGTCTTC
     CysSerThrValLeuProLeuTyrHisLysTyrIleLeuPheCysThrThrValPhe  211

654 ACCCTGCTCCTGCTTTCCATCGTCCTTCTACTGCAGGATCTACTCCTTGGTGAGGACT
     ThrLeuLeuLeuSerIleValIleLeuTyrCysArgIleTyrSerLeuValArgThr  231

714 CGAAGCCGCCGCCTGACCTTCCGCAAGAACATCTCCAAGGCCAGCCAGTTCCGAGAAG
     ArgSerArgArgLeuThrPheArgLysAsnIleSerLysAlaSerArgSerGluLys  251

774 TCTCTGGCCTTGCTGAAGACAGTGATCATTGTCCTGAGTGTCTTCATTGCCTGCTGGGCC
     SerLeuAlaLeuLeuLysThrValIleIleValLeuSerValPheIleAlaCysTrpAla  271

834 CCTCTCTTCATCCTACTACTTTTAGATGTGGGGTGCAAGGCGAAGACCTGTGACATCCTG
     ProLeuPheIleLeuLeuLeuAspValGlyCysLysAlaLysThrCysAspIleLeu  291

894 TACAAAGCAGAGTACTTCCTGGTTCTGGCTGTCCTGAACTCAGTGACCAACCCCATCATC
     TyrLysAlaGluTyrPheLeuValLeuAlaValLeuAsnSerGlyThrAsnProIleIle  311

954 TACACTCTGACCAATAAGGAGATGCGCCGGGCCTTCATCAGGATCATATCTTGTTGCAAA
     TyrThrLeuThrAsnLysGluMetArgArgAlaPheIleArgIleIleSerCysCysLys  331

1114 TGCCCCAACGGAGACTCCGCTGGCAAATTCAAGAGGCCCATCATCCCGGGCATGGAATTT
     CysProAsnGlyAspSerAlaGlyLysPheLysArgProIleIleProGlyMetGluPhe  351

1194 AGCCGCAGCAAATCAGACAACTCCTCCCACCCCAGAAGGATGATGGGACAATCCAGAG
     SerArgSerLysSerAspAsnSerSerHisProGlnLysAspAspGlyAspAsnProGlu  371

1254 ACCATTATGTCTTCTGAAACGTCAATTCTTCTTCTTAAAACCGAAGCTGTTGATACTG
     ThrIleMetSerSerGlyAsnValAsnSerSerSer***  383
```

FIG. 7B

```
1314 TTGATTCTGGCTTCATCACTCACTACCCTAGCATTTCAAAAACATCTCTCTTCTCCACT
1374 GCTGCAAGGAAGAAGCAGCCGGGAGCCTGAGAGAGGAAGGAGGAAGGAGAGAATGTGCGGCTT
1434 GGTGATACCATGTTGTAGGTAGGTTATGATTATGAACAATGCCCTGGAAGGGTGGAGAT
1494 CAGATCTGCCTGCAGAGGGTTCCTGCCCCTAATCTCTTCACTTCCTTCAGTCGTT
1554 TCTGTTTATCCCCATACTCTTTTTCCCGTTTTTCTCATTCCCCTCTCTACC
1614 ATCGCTTTCTTTCTCTTTCTTTAAATTTAGGGGCAAACAAAAGGAATCCCACAAATGGA
1674 TATTGTGAAAACATAGTGCTGAATGACGGCAAAGAATGGTAAATCAAAGATAAAT
1734 TAACTTCATAAGACTGCTATTCTGAAATGCAACAATCTTGTACAGTCAGGACTGATAAAA
1794 TGGAGCAATACAGATCAGACATTTCAGATGCCCGTCAATGTAAAAATCACCTACTTGAACATTGTAT
1854 GCAATACATTCACACACAAAAGCAATACTGTAGCCCTTATTGAACAATACTGAACTCAT
1914 AAATACTCATGGTTTCACTCTGCCTGTCCAGGCCCTAAGGACTATGCTGCTGTAATACAGGAA
1974 AACACAGGATGCCCTCACTCCTATTAAAAATGTCACTCAAGAAAAGTCTCTTGTAACGTAAA
2034 GGCAAACACATGTAGCTACTGAGCTATGACTGAGCTATGACTGAGGTGAGCACACTCTATGGGAAAACA
2094 CCGGACTCCAC
```

FIG. 7C 5,585,476

MOLECULAR CLONING AND EXPRESSION OF G-PROTEIN COUPLED RECEPTORS

This invention was made with government support under the National Institute on Drug Abuse grant number DA07244. The government has certain rights in this invention.

BACKGROUND OF THE INVENTION

The development of multicellular organisms requires the orchestration of many precisely coordinated events involving cell-type specific growth, proliferation, differentiation, migration, and cell death. Not surprisingly, intercellular communication plays critical roles in these processes. Although the molecular mechanisms involved in this communication are in general poorly understood, this research field is characterized by increasingly rapid progress initiated by the realization that viral oncogenes are, in many cases, transformed versions of cellular genes (proto-oncogenes) that participate in the intercellular communication directing development. Furthermore, it has been established that many non-viral forms of cancer also result from transformation of genes involved in signal transduction (e.g. growth factors, growth factor receptors, and transcription factors).

A large number of mammalian growth factor receptors have been cloned and many are recognized proto-oncogenes (Yarden and Ullrich, 1988). Most of these cloned receptors are members of a superfamily of integral membrane proteins with intrinsic, growth factor-inducible, tyrosine kinase activity. An extensive research literature now documents the critical roles these receptors play in cell proliferation, differentiation, and malignant transformation. However, multiple lines of evidence suggest that members of the G-protein coupled receptor (GPR) superfamily may also participate in mammalian development and oncogenesis. For example, both the yeast S. cerevisiae and the slime mold D. discoideum express GPRs that regulate cell differentiation (Devreotes, 1989; Sprague, 1991). In addition, mammalian mitogenesis and cell proliferation are affected by several peptides and neurotransmitters which are known to interact with GPRs (Hanley, 1989; Zachary et at., 1987).

Perhaps the most direct evidence linking GPRs with ontogeny and cancer has been provided by the ectopic expression of GPRs in tissue culture cells. Thus, the mas oncogene encodes a putative GPR ($p^{mas}$) and leads to malignant transformation when transfected into NIH3T3 mouse fibroblasts cells (Young et al., 1986). In addition, several serotonin and muscarinic acetylcholine receptors (all GPRs) also produce this malignant transformation if ectopically expressed in NIH3T3 cells and stimulated by their respective ligands (Gutkind et al., 1991; Julius et al., 1989; Julius et al., 1990). While these data illustrate that GPRs can greatly influence cell proliferation and morphology, the GPRs that were studied are unlikely to be involved in these processes in vivo because they reside in fully differentiated, postmitotic cells such as neurons where serotonergic receptors, muscarinic receptors, and most likely $p^{mas}$ regulate the changing electrical properties of neuronal membranes involved in neurotransmission. However, these data support the possibility that other GPRs are expressed in vivo in immature cells where they regulate proliferation and differentiation. Furthermore, these data suggest that some forms of cancer may result from mutations or viral infections that lead to improper functioning, activation, or expression of such GPRs. Thus, identification and characterization of such receptors should significantly advance both the study of normal development as well as the search for diagnostic and therapeutic tools in oncology.

BRIEF SUMMARY OF THE INVENTION

The subject invention concerns the cloning and sequencing of cDNAs and the proteins encoded by those cDNAs. The cDNAs encode novel polypeptides that are members of the G-protein coupled receptor (GPR) superfamily. The proteins encoded by the DNAs of the subject invention are involved in the regulation of cell proliferation and/or differentiation in vivo. The subject protein receptors are endogenously expressed in various tissues and cell lines.

Specifically, the subject invention concerns the cloning and sequencing of a rat cDNA (H218) that encodes a novel GPR designated $p^{H218}$. Further included in the subject invention are mammalian homologs, including the human homolog of the H218 cDNA. The H218 cDNA was used to determine that H218 mRNA is expressed in all developing organs tested and in seven out of seven cell lines tested. In addition, in the brain, H218 mRNA is much more highly expressed during a period of extensive proliferation and differentiation (embryogenesis) than a period of very limited cell proliferation and differentiation (adulthood), suggesting that $p^{H218}$ does not function as a neurotransmitter receptor. Rather, $p^{H218}$ functions as a growth factor ligand receptor.

The subject invention further concerns antibodies from animals immunized with peptides derived from $p^{H218}$ GPR. Purified antibody made against one of the peptides recognizes a protein having an apparent molecular weight of 50–55 kDA as determined by Western blot analysis.

The subject invention also concerns cDNA of the rat-edg gene. Rat-edg cDNA encodes a GPR, $p^{rat-edg}$. The $p^{rat-edg}$ can be activated by some of the same ligand(s) that activate $p^{H218}$. By identifying compounds that specifically activate or inhibit this class of receptors one can develop unique, pharmaceutical therapies that effectively treat some forms of cancer.

A further aspect of the subject invention concerns polynucleotide molecules that are antisense to mRNA of H218 and rat-edg. The antisense polynucleotide molecules can be used to reduce or inhibit the expression of the subject protein by binding to the complementary mRNA transcripts.

The subject invention also concerns methods of use for the polynucleotide sequences, the encoded proteins, peptide fragments thereof, polynucleotide molecules that are antisense to the H218 and rat-edg sequences, and antibodies that bind to the proteins and peptides. Such use includes diagnostic and therapeutic applications of the subject invention.

BRIEF DESCRIPTION OF THE DRAWINGS

FIG. 1 shows the nucleotide and deduced amino acid sequence of H218 cDNA. The sequence was compiled from that of "H2" cDNA (nucleotides 16 to 2505) and "18" cDNA (nucleotides −155 to 288) which are identical throughout the region of overlap. A black box highlights the optimal consensus sequence for translation initiation. A potential polyadenylation signal is double-underlined and a consensus sequence associated with mRNA instability is boxed. Repetitive nucleic acid sequences in the 3' untranslated region are underlined. An arrow designates a predicted N-glycosylation site. A consensus sequence for proline directed kinases is underlined with a broken line. Brackets below the amino acid sequence indicate possible nucleotide binding site components in the carboxy-terminal and "third cytoplasmic loop" domains respectively.

FIG. 7 shows the nucleotide and deduced amino acid sequence of rat-edg cDNA. An ATTTA motif is boxed in black.

BRIEF DESCRIPTION OF THE SEQUENCES

SEQ ID NO. 1 is the nucleotide sequence of the $^{H218}$ cDNA.

SEQ ID NO. 2 is the deduced antino add sequence of the $p^{H218}$ protein encoded by the H218 cDNA SEQ ID NO. 3 is the nucleotide sequence of the rat-edg cDNA.

SEQ ID NO. 4 is the deduced amino acid sequence of the $p^{rat-edg}$ protein encoded by the rat-edg cDNA.

SEQ ID NO. 5 is the amino acid sequence of a synthetic $p^{H218}$ peptide designated peptide 1.

SEQ ID NO. 6 is the amino acid sequence of a synthetic $p^{H218}$ peptide designated peptide 2.

SEQ ID NO. 7 is the amino acid sequence of a synthetic $p^{H218}$ peptide designated peptide 3.

SEQ ID NO. 8 is the amino acid sequence of a synthetic $p^{H218}$ peptide designated peptide 4.

SEQ ID NO. 9 is the amino acid sequence of a D2 dopaminergic receptor.

SEQ ID NO. 10 is the amino acid sequence of a β2 adrenergic receptor.

SEQ ID NO. 11 is the amino acid sequence of a α2 adrenergic receptor.

SEQ ID NO. 12 is the amino acid sequence of a 1A serotonergic receptor.

SEQ ID NO. 13 is the amino acid sequence of a M1 muscarinic receptor.

SEQ ID NO. 14 is the amino acid sequence of a substance K receptor.

DETAILED DISCLOSURE OF THE INVENTION

The subject invention concerns novel cDNAs (H218 and rat-edg) that encode G-protein coupled receptors. The proteins, designated $p^{H218}$ and $p^{rat-edg}$, play important roles in cell proliferation and differentiation, and in disease states such as cancer.

The H218 cDNA has been sequenced (SEQ ID NO. 1) and the amino acid sequence of the polypeptide that it encodes determined (SEQ ID NO. 2) (FIG. 1). The H218 cDNA contains a 1056 bp open reading frame that encodes a polypeptide of 352 amino acids. The 3' untranslated region of H218 cDNA contains repetitive sequences, a consensus sequence for mRNA instability, and a series of terminal adenosines preceded by a potential polyadenylation site. The predicted cytoplasmic regions of $p^{H218}$ contain potential nucleotide binding site components and a consensus sequence for proline directed kinases involved in cell division and growth factor responses.

Figure 2A:
FIG. 2 shows a comparison of $p^{H218}$ with other G-protein coupled receptors. Black boxes highlight residues identical to $p^{H218}$ residues. D2=D2 dopaminergic receptor; β2=β2 adrenergic receptor; α2=α2 adrenergic receptor; 5HT1A= 1A serotonergic receptor; M1=M1 muscarinic receptor; SK= substance K receptor. The numbers in parentheses indicate the number of omitted residues.

Analysis of the deduced amino acid sequence of $p^{H218}$ revealed that it is a member of the GPR superfamily (FIG. 2). Several features of $p^{H218}$ are common to all other GPRs, including: 1) seven regions of hydrophobicity which are predicted to act as membrane spanning domains, 2) a consensus sequence for N-linked glycosylation in its predicted N-terminal extracellular domain, and 3) a conserved cysteine residue and several serine and threonine residues in its predicted intracellular C-terminal domain. In addition, $p^{H218}$ contains many other residues which are highly conserved among most GPRs. However, $p^{H218}$ is distinct from these GPRs in that it does not contain certain highly conserved residues. Perhaps most notable are the aspartate and tyrosine residues at the cytoplasmic end of the third transmembrane domain, and the cysteine residue at the extracellular end of the same transmembrane domain.

$p^{H218}$ affects the course of cellular proliferation and/or differentiation events. Of all cloned proteins, $p^{H218}$ is most homologous to human $p^{edg}$, a putative GPR implicated in endothelial cell differentiation. The possibility of a direct interaction between $p^{H218}$ and growth-related intracellular proteins is suggested by the similarity between the predicted cytoplasmic region of $p^{H218}$ and motifs of the src homology domain 2 (SH2) found in many cytoplasmic proteins that are critically involved in growth-related signal transduction, including several proteins encoded by oncogenes.

A further aspect of the subject invention concerns polynucleotide molecules which encode the human homolog of the rat H218 gene. Human cDNAs that hybridize with H218 cDNA were isolated from a human embryonic brain cDNA library. These polynucleotide molecules can be used to express the human counterpart of $p^{H218}$. Antibodies can then be raised against the expressed protein, or peptide fragments thereof. The polynucleotide molecules, proteins, and antibodies of the human homolog of $p^{H218}$ can be used in both diagnostic and therapeutic applications.

A further aspect of the subject invention concerns antibodies raised against synthetic peptides of $p^{H218}$. These peptides, designated as 1, 2, 3, and 4 (and corresponding to SEQ ID NO. 5, SEQ ID NO. 6, SEQ ID NO. 7, and SEQ ID NO. 8, respectively), correspond to separate extracellular and intracellular regions of $p^{H218}$. These peptides and their amino acid sequence are shown in Table 1.

TABLE 1

Amino Acid Sequences of $p^{H218}$ peptides

| $p^{H218}$ peptide | Sequence |
| --- | --- |
| peptide 1 | SEQ ID NO. 5 KETLDMQETPSR |
| peptide 2 | SEQ ID NO. 6 YSEYLNPEKVQE |
| peptide 3 | SEQ ID NO. 7 RQGKGATGRRGG |
| peptide 4 | SEQ ID NO. 8 RSSSSLERGLHM |

Polyclonal antibodies that react with the antigen peptides were raised in rabbits immunized with the respective peptide. Each antibody recognizes by an ELISA assay the specific peptide used as the immunogen. One of the antibodies, from a rabbit immunized with peptide 1 (SEQ ID NO. 5), was affinity purified and used in a Western blot with antigens from a cell line that expresses H218 mRNA. This antibody recognized a band of 50 to 55 kDa, and a band of 180 to 200 kDa in the Western blot. These antibodies can be used for detecting and purifying the $p^{H218}$ protein through standard procedures known in the art. The antibodies can also be used for localization of $p^{H218}$ in tissues using immunohistochemical techniques known in the art.

The subject invention further contemplates the use of the protein and peptides to generate both polyclonal and monoclonal antibodies. Thus, monoclonal antibodies to $p^{H218}$, and peptide fragments thereof, can be produced using the teachings provided herein in combination with procedures that are well known in the art. Such antibodies can be produced in several host systems, including mouse, rat, and human.

Also included within the scope of the invention are binding fragments of the antibodies of the subject invention. Fab', F(ab')$_2$, and Fv fragments may be obtained by conventional techniques, such as proteolytic digestion of the antibodies by papain or pepsin, or through standard genetic engineering techniques using polynucleotide sequences that encode binding fragments of the antibodies of the subject invention.

A further aspect of the subject invention concerns the cloning and sequencing of the rat homolog of the human edg gene, which also encodes a GPR. This rat gene, designated rat-edg, is similar in sequence to the human edg gene. The rat-edg cDNA (SEQ ID NO. 3) encodes a protein, $p^{rat-edg}$ (SEQ ID NO. 4). The $p^{rat-edg}$ protein also has several features in common with other members of the GPR superfamily including 1) seven hydrophobic regions presumed to act as transmembrane domains, 2) a putative N-glycosylation site in the N-terminal domain, 3) putative phosphorylation sites in cytoplasmic domains, and 4) a conserved cysteine residue in the C-terminal domain.

The subject invention also concerns polynucleotide molecules having sequences that are antisense to mRNA transcripts of H218 and rat-edg polynucleotides. An administration of an antisense polynucleotide molecule can block the production of the protein encoded by H218 or rat-edg. The techniques for preparing antisense polynucleotide molecules, and administering such molecules are known in the art. For example, antisense polynucleotide molecules can be encapsulated into liposomes for fusion with cells.

As is well known in the art, the genetic code is redundant in that certain amino acids are coded for by more than one nucleotide triplet (codon). The subject invention includes those polynucleotide sequences which encode the same amino acids using a different codon from that specifically exemplified in the sequences herein. Such a polynucleotide sequence is referred to herein as an "equivalent" polynucleotide sequence. Thus, the scope of the subject invention includes not only the specific polynucleotide sequences depicted herein, but also all equivalent polynucleotide sequences encoding the polypeptides of the subject invention, and fragments or variants thereof.

The polynucleotide sequences of the subject invention can be prepared according to the teachings contained herein, or by synthesis of oligonucleotide fragments, for example by using a "gene machine" using procedures well known in the art.

The polypeptides of the subject invention can be prepared by expression of the cDNAs in a compatible host cell using an expression vector containing the polynucleotide sequences of the subject invention. The polypeptides can then be purified from the host cell using standard purification techniques that are well known in the art. Alternatively, the polypeptides of the subject invention can be chemically synthesized using solid phase peptide synthesis techniques known in the art.

The polypeptides of the subject invention can be used as molecular weight markers, as an immunogen for generating antibodies, and as an inert protein in certain assays. The polynucleotide molecules of the subject invention can be used as DNA molecular weight markers, as a chromosome marker, and as a marker for the gene on the chromosome.

The term "polynucleotide sequences" when used in reference to the subject invention can include all or a portion of the cDNA. Similarly, polynucleotide sequences of the subject invention also includes variants, including allelic variations or polymorphisms of the genes. The polynucleotide sequences of the invention may be composed of either RNA or DNA. More preferably, the polynucleotide sequences of the subject invention are composed of DNA.

As used herein, the term "isolated" means, in the case of polynucleotide sequences, that the sequence is no longer linked or associated with other polynucleotide sequences with which it would naturally occur. Thus, the claimed polynucleotide sequences can be inserted into a plasmid or other vector, to form a recombinant DNA cloning vector. The cloning vector may be of bacterial or viral origin. The vector may be designed for the expression of the polypeptide encoded by the polynucleotide sequence. The vector may be transformed or transfected or otherwise inserted into a host cell. The host cell may be either prokaryotic or eukaryotic, and would include bacteria, yeast, insect cells, and mammalian cells. For example, a bacterial host cell may be *E. coli*, and a mammalian host cell may be the PC12 cell line.

As used herein, the term "isolated" means, in the case of proteins, obtaining the protein in a form other than that which occurs in nature. This may be, for example, obtaining $p^{H218}$ by purifying and recovering the protein from a host cell transformed to express the recombinant protein. In the case of antibodies, "isolated" refers to antibodies, which, through the hand of man, have been produced or removed from their natural setting. Thus, isolated antibodies of the subject invention would include antibodies raised as the result of purposeful administration of the proteins, or peptide fragments thereof, of the subject invention in an appropriate host.

The various genetic engineering methods employed herein are well known in the art, and are described in Sambrook, J., et al. (1989) *Molecular Cloning: A Laboratory Manual*, Cold Spring Harbor Laboratory, New York. Thus, it is within the skill of those in the genetic engineering art to screen cDNA libraries, perform restriction enzyme digestions, electrophorese DNA fragments, tail and anneal vector and insert DNA, ligate DNA, transform or transfect host cells, prepare vector DNA, electrophorese proteins, sequence DNA, perform Northern, Southern and Western blotting, and perform PCR techniques.

Materials and Methods

Cloning of H218 cDNA. A "LAMBDA ZAP" cDNA library (Stratagene, La Jolla, Calif.) constructed using rat hippocampal RNA was screened at medium stringency with a 926 bp 5' EcoRI-Bgl II 3' fragment of a D2 dopamine receptor cDNA (MacLennan et al., 1990). The cDNA was labeled with $^{32}$P by random hexamer priming. Nitrocellulose filters were incubated for 2 hrs at 42° C. in 5X SSPE (1X SSPE=0.15M NaCl, 12 mM NaH$_2$PO$_4$H20, 1mM EDTA, pH 7.4), 40% formamide, 0.15% SDS, 5X Denhardt's solution, 100 µg/ml denatured salmon sperm DNA, and 2 µg/ml polyadenylic acid. The filters were then incubated overnight in the same solution at 42° C. with the probe added (approximately 10$^6$ cpm/ml). The filters were washed two times for 15 minutes each at room temperature in 2X SSC (standard saline citrate buffer: 1X SSC=0.15M NaCl, 0.015M sodium citrate, pH 7.2), followed by two washes for 45 minutes each at 42° C. in 2X SSC.

In order to exclude D2 receptor cDNAs from analysis, all hybridizing phage were screened at high stringency with four oligodeoxynucleotide probes designed to specifically recognize D2 dopamine receptor cDNAs (MacLennan et al., 1990). All phage that hybridized to the oligonucleotides were eliminated from further rounds of purification. All other phage that hybridized to the cDNA probe were purified, converted into "BLUESCRIPT" plasmids (Stratagene) according to the manufacturer's automatic excision protocol, and evaluated by restriction digests and gel electrophoresis. Sequence analysis revealed that one of the hybridizing cDNAs, designated "H2", encodes a portion of a putative G-protein coupled receptor (GPR), based on sequence comparisons to other GPRs.

A modified polymerase chain reaction (PCR) technique was used to clone the 5' cDNA for the H218 cDNA (Loh et al., 1989). H2 cDNA extends 2.6 kb to a 5' end that encodes part of the presumed extracellular N-terminal domain of the receptor. Thus, an oligodeoxynucleotide corresponding to the antisense strand of H2 (nucleotides 288 to 312 of H218) primed the first strand cDNA synthesis with M-MLV Reverse Transcriptase (Gibco-BRL, Gaithersburg, Md.). Poly-A RNA extracted from postnatal day 14 (P14) rat lung served as a template. Terminal Deoxynucleotidyl Transferase (Gibco-BRL) was used to "tail" the resulting cDNA with guanines. The cDNA was then subjected to 35 rounds of PCR amplification with "AMPLITAQ" DNA polymerase (Perkin-Elmer, Branchburg, N.J.) The reaction was primed with an internal H2 specific primer containing antisense strand nucleotides 263 to 288 of H218 and a primer containing a poly-cytosine sequence. The resulting "18" cDNA was subcloned into a "BLUESCRIPT" plasmid (Stratagene) by exploiting restriction sites designed into the 5' ends of the PCR primers.

The "H2" and "18" cDNA fragments were then spliced together to form a 2.75 kb cDNA (designated "H218") containing a complete open reading frame (ORF) of 1052 bp that encodes a polypeptide of 352 amino acids.

Characterization of cDNA Clones The nucleotide sequences of both strands of the H218 cDNA were determined by the dideoxy chain termination technique (Sanger et at., 1977). The T7 Sequencing kit (Pharmacia, Piscataway, N.J.) was used with denatured, double-stranded cDNAs in "BLUESCRIPT" plasmids serving as templates.

Tissue Preparation For RNA preparations, Long Evans rats were killed by decapitation and their brains were immediately removed and dissected. Individual brain regions were frozen in liquid nitrogen. Rats and embryos of both sexes were used in the developmental study. Brains taken from embryos are designated with an "E" and those taken postnatally are designated with a "P". For example, a brain removed 20 days after birth would be P20.

RNA Preparation, Electrophoresis, and Blotting Frozen, dissected brain regions were pooled. The "FASTTRACK" kit (Invitrogen Corp., San Diego, Calif.) was used to extract Poly-A RNA from tissue culture cells and brain tissue used in the developmental study. Total RNA was extracted by homogenization in 4M guanidine thiocyanate followed by centrifugation through 5.7M CsCl according to the method of Chirgwin (Chirgwin et al., 1979). The RNA was purified by repeated ethanol precipitations, and its concentration was estimated spectrophotometrically from $A_{260}$. All RNA samples were stored at −20° C. as ethanol precipitates.

RNA (1–10 µg of Poly-A or 20 µg of total) was denatured in 50% deionized formamide, 6.0% formaldehyde at 65° C. for 5 min and then size-fractionated by electrophoresis on a horizontal agarose gel (1.25%) containing 6.0% formaldehyde. The RNA was subsequently transferred to nylon membranes (ICN BIOTRANS membrane), which were then dried and baked at 80° C. for 2 hours under vacuum. Membranes were prehybridized for 2 hrs at 42° C. in 5X SSC, 50% formamide, 0.5% SDS, 50 mM sodium phosphate (pH 6.5) containing 250 µg/ml denatured salmon sperm DNA, 5X Denhardt's solution, and 100 µg/ml polyadenylic acid. The H2 cDNA probe was then $^{32}$P-labeled by random hexamer priming, and added to the prehybridization solution. After hybridization at 42° C. overnight, the membranes were washed twice for 30 min at room temperature in 2X SSC and twice for 45 min at 60° C. in 0.1X SSC, 0.1% SDS.

Membranes were exposed to X-ray film with two intensifying screens at −80° C. for several different time intervals in order to ensure that all comparisons were made within the linear sensitivity range of the film. The probe was then removed from the membranes by washing at 65° C. in 50% formamide, 10 mM sodium phosphate, pH 6.5%, for 1 hour. Stripped blots were rinsed in 2X SSC, 0.1% SDS and exposed to film to check for complete removal of probe. To correct for possible intersample variability in extraction, loading, or transfer of the RNA, the membranes were probed with $^{32}$P-labeled rat cDNA that recognizes ribosomal RNA or with a rat cyclophilin cDNA. Brain cyclophilin mRNA levels are reported to be stable during brain development (Danielson et al., 1988).

Tissue Culture Cells were grown on plates in Dulbecco's Modified Eagle Media (DMEM) containing 10% fetal bovine serum (FBS), with the exception of PC12 cells which were grown in RPMI media containing 10% horse serum and 5% FBS. Tissue culture cells were washed with 1X PBS, pH 7.4 while anchored to plates, mechanically dislodged, and collected by centrifugation for RNA extraction.

Antibody Production Four peptides having amino acid sequences based on the deduced sequence of $p^{H218}$, and that correspond to separate extracellular and intracellular regions of $p^{H218}$ were synthesized by the Interdisciplinary Center for Biotechnology Research Core lab at the University of Florida. Rabbits were immunized with the peptides and antiserum prepared according to standard methods. Antisera (designated "IA") from the rabbit immunized with peptide 1 (SEQ ID NO. 5) was purified by precipitation with 4.1M saturated ammonium sulfate at 25° C. overnight. The precipitate was dissolved in PBS and dialyzed against several changes of PBS. The 1A antibody was then affinity purified over a CNBr-Sepharose affinity column (Sigma Chemical, St. Louis, Mo.) to which the peptide 1 (SEQ ID NO. 5) had been attached. Antibody was eluted with 0.1M glycine, pH 2.5.

Western Blotting Crude cellular protein extract or membrane preparations from cell lines that express H218 mRNA were loaded onto a SDS-PAGE gel and electrophoresed. The proteins were then transferred to nitrocellulose paper and reacted with a 1:500 dilution of purified antibody. Rabbit antibody was then detected with a labeled second-step reagent specific for rabbit antibody.

Cloning of the rat-edg cDNA A 1241 bp EcoRI-BamHI fragment of H2 cDNA was labeled with $^{32}P$ by random hexamer priming and used to screen approximately $7.5 \times 10^5$ cerebellar cDNAs of a rat cerebellar 2-ZAP library at medium stringency. The final hybridization wash was for 45 minutes at 47° C. in 2X SSC. Hybridizing clones were isolated for further evaluation. Purified clones were transferred into "BLUESCRIPT" plasmids (Stratagene) according to the manufacturer's protocol. Denatured double-stranded plasmids were sequenced by the dideoxy chain termination method (Sanger et al, 1977).

The following are examples which illustrate procedures and processes, including the best mode, for practicing the invention. These examples should not be construed as limiting, and are not intended to be a delineation of all possible modifications to the technique. All percentages are by weight and all solvent mixture proportions are by volume unless otherwise noted.

Example 1-Cloning and Sequence Analysis of H218

A rat hippocampal cDNA library was screened at medium stringency with a rat D2 dopamine receptor cDNA. One of the hybridizing cDNAs, designated "H2", encodes all but a few amino-terminal residues of a novel G-protein coupled receptor. A cDNA, designated "18", encoding the remaining amino-terminal residues was isolated using a modified PCR technique. The H218 cDNA was prepared from the two independent, overlapping cDNA clones "H2" and "18" which were isolated as described above. The H2 and 18 cDNAs were spliced together to yield a 2.75 kb cDNA containing a complete 1056 bp ORF encoding 352 amino acids. The corresponding gene will be referred to herein as H218, and the encoded GPR protein as $p^{H218}$. The nucleotide sequence and the amino acid sequence that it encodes are shown in FIG. 1. The series of cytosines at the 5' end of the clone result from the PCR procedure used to isolate the "18" cDNA. A database search revealed that $p^{H218}$ is clearly a member of the GPR superfamily (FIG. 2).

Example 2-H218 mRNA Expression in Brain Tissue

Figure 3A:
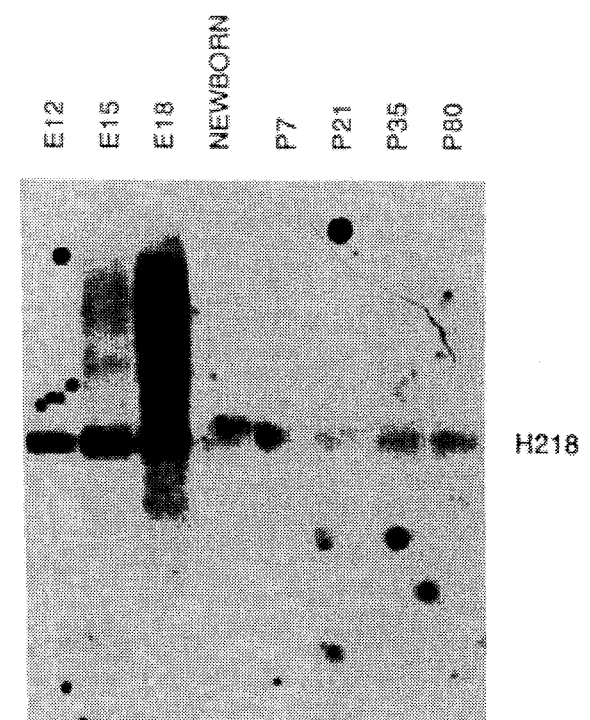
FIG. 3 shows an X-ray autoradiograph of a Northern blot illustrating the ontogenic regulation of H218 mRNA levels in the rat brain. Poly-A RNA was extracted from whole rat brain at embryonic days 12, 15, 18, Birth, postnatal days 7, 21, 35, and 80 (adult). The resulting blot was probed for H218 mRNA (panel A), stripped, and then probed with a cyclophilin cDNA (panel B) to control for variation in extraction, loading, and transfer (brain cyclophilin mRNA levels are reported to be stable from E12 to adult). The relative intensity of the cyclophilin bands have consistently paralleled results obtained from probing the same blots with an oligo-dT probe designed to hybridize to all mRNA poly-A tails.
Figure 3B:
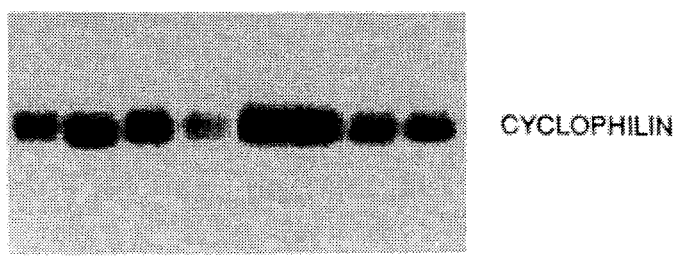

Poly-A RNA was extracted from whole rat brain at multiple stages of development ranging from embryonic day 12 (E12) to postnatal day 80 (P80; adult). A Northern blot of the rat RNA was probed with the complete H2 cDNA. The blot was washed at progressively higher stringencies and exposed to X-ray film after each wash. The autoradiograph revealed an approximately 3.2 kb transcript at all stages of development (FIG. 3). However, H218 mRNA levels are much higher during brain embryogenesis than during later periods of brain development. This pattern indicates that H218 plays a role in cell proliferation and/or differentiation, which is prevalent during brain embryogenesis, rather than in neurotransmission, which is prevalent later in brain development. However, the H218 gene may be involved during all of these processes.

The autoradiographs following the high stringency wash also contain other bands and/or smears, primarily in the E15 and E18 lanes. These signals displayed a preferential reduction in intensity (relative to the 3.2 kb band) during the series of progressively higher stringency washes leading up to the high stringency wash. Therefore, they most likely represent DNA contamination and/or abundant cross hybridizing mRNAs that are related, but not identical, to H218 mRNA. It is also possible that they may partially represent additional ontogenetically regulated H218 transcripts. However, in a smaller scale Northern blot experiment which examined only E15, E18, and P14 brain H218 mRNA, a single 3.2 kb band at E15 and E18 was detected.

Example 3-H218 mRNA Expression in Other Tissue

Figure 4A:
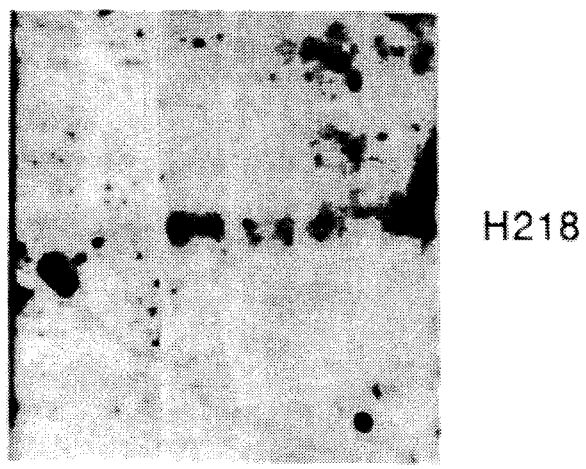
FIG. 4 shows an X-ray autoradiograph of a Northern blot illustrating the distribution of H218 mRNA in various tissues of the postnatal day 14 rat. Approximately 20 fig of total RNA was loaded per lane. The blot was probed for H218 mRNA (panel A), stripped, and then probed for rat ribosomal RNA (panel B) as an extraction, loading, and transfer control.
Figure 4B:
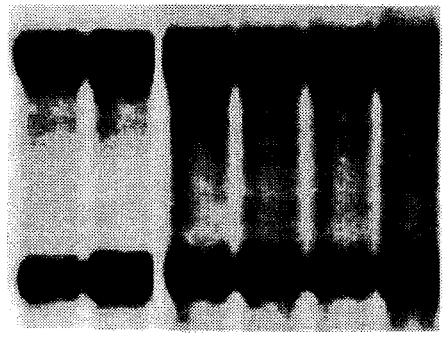

A Northern blot analysis of total RNA extracted from various organs of the postnatal day 14 (P14) rat was performed. The blot was probed with the H2 cDNA and washed at high stringency. A 3.2 kb H218 mRNA transcript was present in all tissues examined (FIG. 4). The H218 mRNA was most abundant in the lung. Less was found in the kidney, gut, and skin. A very low level of expression was detected in the spleen, brain and liver. This widespread distribution of H218 mRNA expression outside the brain at this stage of development is consistent with $p^{H218}$ role in cell proliferation and/or differentiation.

Example 4-H218 mRNA Expression in Cell Lines

Northern blots were performed using poly-A RNA extracted from seven cell lines. The blots were probed with the H2 cDNA, washed at high stringency, and exposed to X-ray film. H218 mRNA was detected in all rodent cell lines examined. Thus, H218 mRNA is synthesized in B104 rat neuroblastoma cells, C6 rat glioma cells, PC12 rat pheochromocytoma cells, NB41A3 mouse neuroblastoma cells, D6P2T rat Schwannoma cells, NIH3T3 mouse fibroblasts, and RJK88 Chinese hamster fibroblasts. In all cases a prominent 3.2 kb band was observed after the high stringency wash, indicating that the sequence and size of the H218 mRNA transcript is highly conserved among mammals. The relative intensity of the band for each cell line is shown in Table 2.

TABLE 2

| Relative H218 mRNA concentrations in cell lines | |
|---|---|
| B104 rat neuroblastoma cells | +++ |
| PC12 rat pheochromocytoma cells | ++ |
| C6 rat glioma cells | +++ |
| D6P2T rat Schwannoma cells | ++ |
| NB41A3 mouse neuroblastoma cells | + |
| NIH3T3 mouse fibroblasts | ++ |
| RJK88 hamster fibroblasts | ++ |

Of the cells lines and tissue samples examined, H218 mRNA is most abundant in the B104 neuroblastoma cells and the C6 glioma cells. The presence of relatively high concentrations of H218 mRNA in these primitive transformed cells further confirms that the H218 gene is expressed in the early stages of development.

Example 5-Manipulation of H218 mRNA levels using PMA and Nerve Growth Factor

Figure 5A:
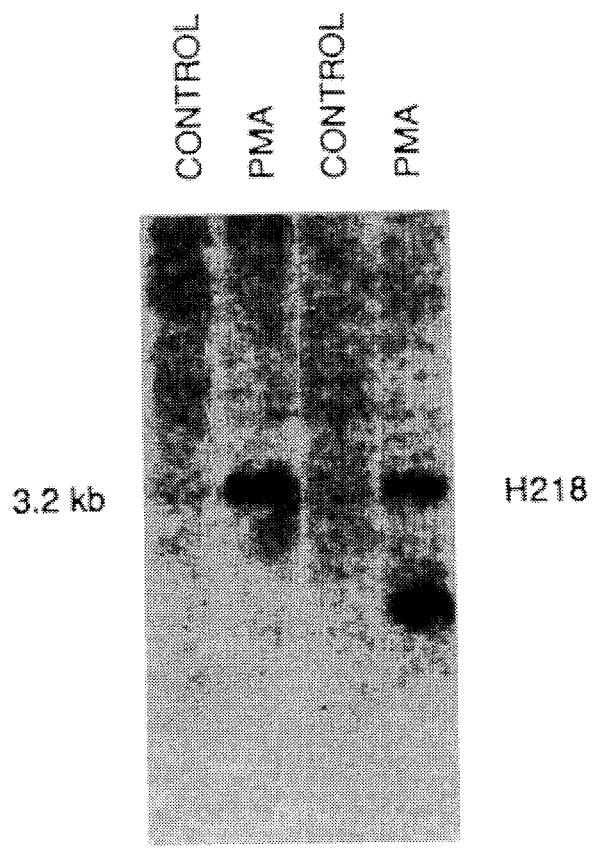
FIG. 5 shows an X-ray autoradiograph of a Northern blot illustrating the effect of PMA treatment on H218 mRNA levels in RJK88 fibroblasts. Poly-A RNA was extracted from 2 independent 100 mm plates of cells treated with PMA for 2 hrs (PMA) or 2 parallel plates of cells treated with vehicle (CONTROL). The resulting blot was probed for H218 mRNA (panel A), stripped, and then probed for cyclophilin mRNA (panel B) as an extraction, loading, and transfer control. Lanes are presented in pairs based on their relative mRNA content (as indicated by the cyclophilin data).
Figure 5B:
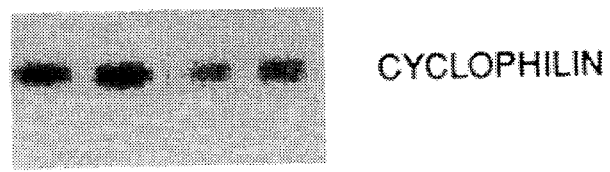

RJK88 Chinese hamster fibroblasts were grown to approximately 80% confluence in Dulbecco's Modified Eagle Media (DMEM) containing 10% fetal bovine serum (FBS). The cells were then "serum-deprived" in DMEM containing 0.5% FBS for 2 days and subsequently treated with phorbol 12-myristate 13-acetate (PMA) at a final concentration of 200 ng/ml. Poly-A RNA was extracted 2 hrs after the initiation of PMA treatment. Control RJK88 cells (processed in parallel with PMA treated cells) were grown, serum-deprived, treated with the vehicle for PMA and extracted. A Nonhem blot performed using the RNA was probed with the H2 cDNA and washed under high stringency conditions. H218 mRNA was undetectable in the serum-deprived, "quiescent" control cells but was clearly present in the cells treated with PMA (FIG. 5).

The nerve growth factor (NGF)-induced differentiation of PC12 rat pheochromocytoma cells from a phenotype resembling proliferating, immature adrenal chromaffin cells to a phenotype resembling differentiated sympathetic neurons has been widely employed as a model of neuronal differentiation. A Northern blot was used to determine whether H218 expression in PC12 cells is affected by NGF stimulation. PC12 cells were grown in RPMI media supplemented with 5% FBS and 10% horse serum. The cells were then serum-deprived in RPMI media containing 0.3% FBS and 0.7% horse serum and treated with NGF (50 ng/ml, 2.5 S) 24 hours later. Poly-A RNA was extracted following 1, 4, or 8 hours of the NGF treatment. Control cells (processed in parallel) were treated identically except they received NGF vehicle instead of NGF. A Northern blot using the RNA was probed with the H2 cDNA and washed at high stringency.

Figure 6A:
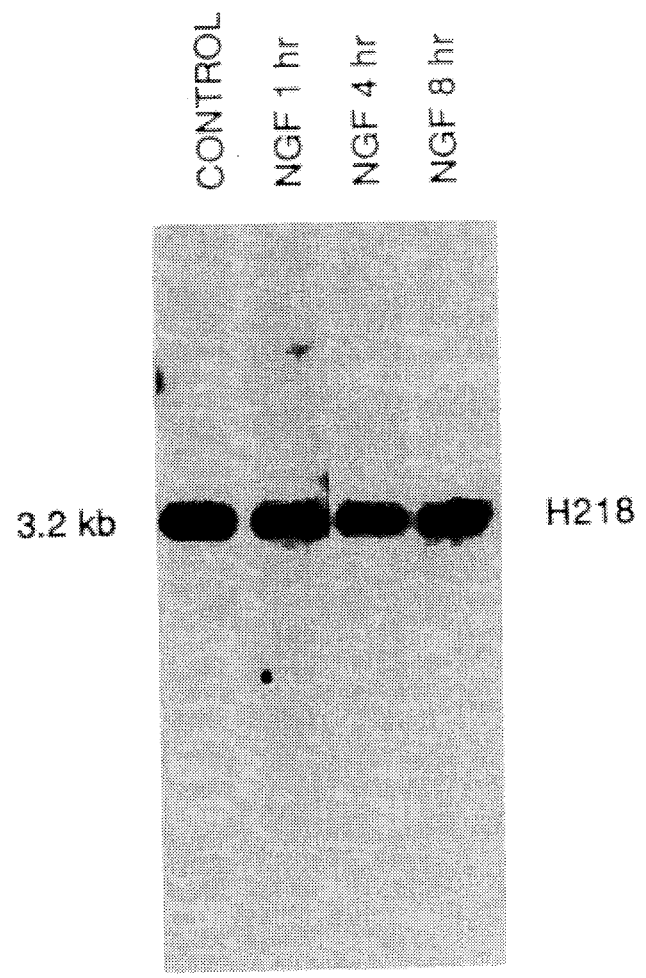
FIG. 6 shows an X-ray autoradiograph of a Northern blot illustrating the effect of NGF treatment on H218 mRNA levels in PC12 cells. Poly-A RNA was extracted from 4 independent 100 mm plates of cells treated with NGF for either 1, 4, or 8 hrs or with a vehicle (CONTROL). The blot was probed for H218 mRNA (panel A), stripped, and then probed for cyclophilin mRNA (panel B) as an extraction, loading, and transfer control.
Figure 6B:
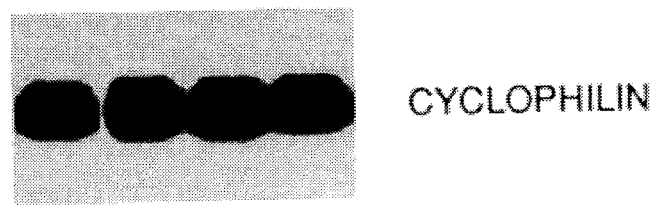

NGF treatment rapidly decreases H218 mRNA concentrations in PC12 cells (FIG. 6). H218 mRNA levels (densitometrically quantitated and normalized to cyclophilin mRNA levels) decreased by 39%, 54%, and 33% following NGF treatment of 1, 4, and 8 hours respectively, but returned to normal by 24 hours of continuous NGF treatment. The apparently transient nature of the H218 mRNA decrease in PC12 cells is unlikely the result of any NGF lability given that 1) NGF is a stable compound in solution and 2) PC12 cells treated with NGF that is only replenished every 2 to 3 days (when the media is exchanged) undergo a continuous differentiation which is reversible upon withdrawal of NGF.

Example 6-Production and Characterization of Anti-$p^{H218}$ Antibodies

Rabbit antisera against four pints-derived synthetic peptides and having the amino acid sequences of SEQ ID NOS. 5, 6, 7, and 8, respectively, were prepared. All antisera specifically recognize, with high titers, the appropriate immunogen peptide by ELISA assay. One of the antisera, designated 1A, has been affinity purified. The purified 1A antiserum recognizes two $p^{H218}$ bands on Western blots of cell lines that express H218 mRNA. Both bands were eliminated when the antiserum was preincubated with the antigen peptide but not when it was preincubated with an equal concentration of an irrelevant control peptide.

In addition, the bands were clearly much more intense from a stable cell line that has been engineered to overexpress $p^{H218}$. The lower (apparent molecular weight of about 50–55 kDa), and weaker, band resulted from monomeric $p^{H218}$ molecules since it roughly corresponds in size to the deduced amino acid sequence encoded by the H218 mRNA open reading frame. The upper (apparent molecular weight of about 180–200 kDa) and more intense band most likely results from an aggregated form of the protein.

The antibody titer in rabbits injected with $p^{H218}$ peptide 1 (SEQ ID NO. 5) rises after the first few injections but drops thereafter, even with continued injections. This unexpected drop was not seen in the rabbits injected with other peptides. It is possible that the drop is the result of the anti-$p^{H218}$ antibodies in the rabbits blocking the function of $p^{H218}$ which, as discussed, may be involved in the cell proliferation events that are required for antibody production.

Example 7-Construction and Characterization of Stable Cell Lines with Increased or Decreased Levels of $p^{H218}$ PC12 cells were transfected with either 1) a vector designed to synthesize H218 mRNA and thereby lead to overexpression of $p^{H218}$, 2) a vector designed to synthesize antisense H218 mRNA and thereby reduce expression of endogenous PC12 cell $p^{H218}$, or 3) the empty vector (as a control). Several stable cell lines derived from each condition were isolated and characterized.

Northern blot analyses indicate that all isolated cell lines designed to overexpress H218 mRNA do express additional H218 mRNA derived from the transfected DNA. The transfected DNA was designed so that the resulting H218 mRNA would differ in size from mature PC12 cell H218 mRNA and therefore can be easily distinguished. Western blot analysis on one of the lines expressing the most H218 mRNA indicate that this line expressed significantly more $p^{H218}$ than vector transfected control lines.

Nerve growth factor (NGF) and basic fibroblast growth factor (bFGF) cause PC12 cells to differentiate from a phenotype resembling proliferating, immature cells to a phenotype resembling differentiated sympathetic neurons. This system has been extensively studied as a model of neuronal development. The effects of NGF and bFGF on our stable cell lines were examined to determine if manipulating $p^{H218}$ levels affects PC12 cell differentiation. The morphology of the cell lines was qualitatively recorded in two identical experiments by an observer unaware of the identity of the cell lines. The two cell lines overexpressing the most H218 mRNA, including the line shown to overexpress $p^{H218}$, displayed a significantly less pronounced, growth factor induced change in cell body morphology when compared to vector transfected controls. Cell lines containing only a small amount of additional (exogenous DNA derived) H218 mRNA, including a line which does not detectably overexpress $p^{H218}$ by Western blot analysis, displayed cell morphology changes indistinguishable from vector transfected controls.

Cell lines transfected with the "antisense" vector displayed a significantly more pronounced growth factor induced change in cell body morphology when compared with vector transfected controls. Therefore, increasing $p^{H218}$ levels decreases differentiation while decreasing the expression of $p^{H218}$ increases cell differentiation.

Example 8-Cloning of Human H218 Homolog

We have screened a human embryonic brain cDNA library using protocols as described for the cloning of the H218 cDNA and have isolated a cDNA which hybridizes under medium stringency conditions (two 45 minute washes at 42° C. in 2X SSC without formamide) to two nonoverlapping fragments of the rat H218 cDNA. The pattern of restriction sites for this novel clone does not match the pattern of restriction sites found with the human edg cDNA clone, and is, therefore, a part of the human homolog of H218.

Example 9-Cloning and Sequence Analysis of rat-edg

A rat cerebellar cDNA library was screened using the H2 cDNA fragment of H218. The largest hybridizing cDNA was completely sequenced (FIG. 7). This 2234 bp cDNA, designated rat-edg, contains a 1149 bp ORF preceded by three in-frame stop codons. The cDNA contains an ATTTA motif in its 3' untranslated region. This motif has been associated with mRNA degradation. The cDNA will subsequently be referred to herein as rat-edg and the encoded protein as $p^{rat-edg}$.

Example 10-Expression of Rat-Edg in RNA in Tissue

The same Northern blot described in Example 2 was stripped and reprobed with the rat-edg cDNA. The blot was then washed at high stringency and exposed to X-ray film. Bands corresponding to an approximately 3.2 kb transcript were visible in all brain regions examined on the resulting autoradiograph. This size is close to the reported 3.0 kb size of human-edg. In contrast to H218 mRNA, the 3.2 kb rat-edg mRNA is preferentially expressed in later stages of postnatal development since a continual increase in mRNA expression is observed throughout development, with highest levels detected at P80. The 3.2 kb band observed following the high stringency wash was not the result of the rat-edg cDNA probe cross-hybridizing to H218 mRNA because: 1) the 3.2 kb transcript recognized by rat-edg displays a pattern of expression which is different from that of H218 mRNA, and 2) the in vitro transcribed H218 and rat-edg RNAs are specifically recognized on Northern blots by the appropriate probes.

A second set of generally weaker bands corresponding to a 4.9 kb transcript was also detected using the rat-edg cDNA. The 4.9 kb bands were not preferentially washed off during a series of progressively higher stringency washes and have been observed in multiple independent experiments. Therefore, they probably reflect an alternative rat-edg gene transcript. Interestingly, the expression of the 4.9 kb rat-edg RNA does not display an obvious trend during the developmental stages examined, and at E18, it is more abundant than the 3.2 kb transcript. In addition, the 4.9 kb rat-edg RNA was detected solely in brain RNA samples.

In addition, a Northern blot was performed with total RNA extracted from several regions of adult rat brain. The blot was probed with the rat-edg cDNA, washed at high stringency, and exposed to X-ray film. Rat-edg mRNA was comparably expressed in every region examined (i.e., the frontal cortex, striatum, ventral forebrain, hippocampus, cerebellum, and substantia nigra/ventral tegmental area). The 4.9 kb transcript may be preferentially expressed in the cerebellum, ventral forebrain, and frontal cortex.

The same Northern blot described in Example 3 was stripped and reprobed with the rat-edg cDNA. The blot was washed at high stringency and exposed to X-ray film. At P14, rat-edg mRNA is expressed in the lung (approximately the same concentration as adult brain) and at a much lower concentration in the liver, spleen, and possibly kidney. However, in contrast to H218 mRNA, rat-edg mRNA was not detected in the gut or skin. As noted above, no 4.9 kb bands are detected in any of these regions although they were visible in lanes of the same Northern that were loaded with brain RNA.

Example 11-Expression of Rat-Edg RNA in Cell Lines

The Northern blots described in Example 4 were stripped and reprobed with rat-edg cDNA. They were subsequently washed at high stringency and exposed to X-ray film. Like H218 mRNA, rat-edg mRNA is expressed in NIH3T3 cells, C6 rat glioma cells, and rat PC12 pheochromocytoma cells. In contrast to H218 mRNA, rat-edg mRNA was not detected in RJK88 hamster fibroblasts, D6P2T rat Schwannoma cells, NB41A3 mouse neuroblastoma cells, or B104 neuroblastoma cells. Only the 3.2 kb transcript was detected in NIH3T3 and C6 cells, while only the 4.9 kb transcript is detected in PC12 cells.

It should be understood that the examples and embodiments described herein are for illustrative purposes only and that various modifications or changes in light thereof will be suggested to persons skilled in the art and are to be included within the scope and purview of this application and the scope of the appended claims.

References

Yarden, Y., A. Ullrich (1988) *Ann. Rev. Biochem.* 57:443–478.

Devreotes, P. (1989) *Science* 245:1054–1058.

Hanley, M. R. (1989) *Nature* 340:97.

Zachary, I., P. J. Woll, E. Rozengurt (1987) *Dev. Biol.* 124:295–308.

Young, D., G. Waitches, C. Birchmeier, O. Fasano, M. Wigler (1986) *Cell* 45:711–719.

Gutkind, J. S., E. A. Novotny, M. R. Brann, K. C. Robbins (1991) *Proc. Natl. Acad. Sci. USA* 88:4703–4707

Julius, D., T. J. Livelli, T. M. Jessell, R. Axel (1989) *Science* 244:1057–1062.

Julius, D., K. N. Huang, T. J. Livelli, R. Axel, T. M. Jessell (1990) *Proc. Natl. Acad. Sci. USA* 87:928–932.

MacLennan, A. J., G. D. Frantz, R. C. Weatherwax, N. J. K. Tillakaratne, A. J. Tobin (1990) *Molec. Cell. Neurosci.* 1:151–160.

Loh, E. By., J. F. Elliot, S. Cwirla, L. L. Lanier, M. M. Davis (1989) *Science* 243:217–220.

Sanger, F., S. Nicklen, A. R. Coulson (1977) *Proc. Natl. Acad. Sci. USA* 74:5463–5467.

Chirgwin, J. M., E. Przbyla, R. J. MacDonald, W. J. Rutter (1979) *Biochem.* 18:5294–5299.

I claim:

1. An isolated polynucleotide molecule selected from the group consisting of a polynucleotide which encodes a $p^{H218}$ polypeptide having the amino acid sequence shown in SEQ ID NO. 2, and a polynucleotide which is antisense to a polynucleotide which encodes a $p^{H218}$ polypeptide having the amino acid sequence shown in SEQ ID NO. 2.

2. An isolated $p^{H218}$ polypeptide having the amino acid sequence shown in SEQ ID NO. 2.

* * * * *

UNITED STATES PATENT AND TRADEMARK OFFICE
CERTIFICATE OF CORRECTION

PATENT NO. : 5,585,476

DATED : December 17, 1996

INVENTOR(S) : Alexander J. MacLennan

It is certified that error appears in the above-identified patent and that said Letters Patent is hereby corrected as shown below:

Column 3, line 23: "20 fig" should read --20 $\mu$g-- line 48: "ATITA" should read --ATTTA-- line 55: "antino" should read --amino--

Column 7, line 27: "$NaH_2PO_4 \cdot H_2O$" should read -- $NaH_2PO_4 \cdot H2O$ --

Column 9, line 12: "(designated "IA")" should read --(designated "1A")-- line 30: "2-ZAP" should read --$\lambda$-ZAP--

Column 11, line 17: "Nonhem" should read --Northern-- line 53: "pints-derived" should read --$p^{H218}$-derived--

Column 13, line 8: "ATITA" should read --ATTTA--

Column 14, line 50: "Loh, E. By.," should read --Loh, E. Y.--

Signed and Sealed this

Thirteenth Day of January, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
  ( A ) LENGTH: 2754 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CCCCCTCGAG | CACAGCCAAC | AGTCACCAAA | GTCAGCCACT | GGCTGTCCCG | GGGCGCAGAC | 60 |
| GCCAAGGCCA | CTCAGGCCAG | GGCAGGGACC | CTGGCCGGCC | TAGCCAGTGC | TCAGTCCCAT | 120 |
| GGCCCCGGCC | GGCCACTGAG | CCCCACCATG | GGCGGTTTAT | ACTCAGAGTA | CCTCAATCCT | 180 |
| GAGAAGGTTC | AGGAACACTA | CAATTACACC | AAGGAGACGC | TGGACATGCA | GGAGACGCCC | 240 |
| TCCCGCAAGG | TGGCCTCCGC | CTTCATCATC | ATTTTATGCT | GTGCCATCGT | GGTGGAGAAC | 300 |
| CTTCTGGTGC | TAATCGCAGT | GGCCAGGAAC | AGCAAGTTCC | ACTCAGCCAT | GTACCTGTTC | 360 |
| CTCGGCAACC | TGGCAGCCTC | CGACCTGCTG | GCAGGCGTGG | CCTTCGTGGC | AACACCTTG | 420 |
| CTCTCCGGAC | CTGTCACCCT | GTCCTTAACT | CCCTTGCAGT | GGTTTGCCCG | AGAGGGTTCA | 480 |
| GCCTTCATCA | CGCTCTCTGC | CTCGGTCTTC | AGCCTCCTGG | CCATTGCCAT | CGAGAGACAA | 540 |
| GTGGCCATCG | CCAAGGTCAA | GCTCTACGGC | AGTGACAAAA | GCTGTCGAAT | GTTGATGCTC | 600 |
| ATTGGGGCCT | CTTGGCTGAT | ATCGCTGATT | CTGGGTGGCT | TGCCCATCCT | GGGCTGGAAT | 660 |
| TGTCTGGACC | ATCTGGAGGC | TTGCTCCACT | GTGCTGCCCC | TCTATGCTAA | GCACTATGTG | 720 |
| CTCTGCGTGG | TCACCATCTT | CTCTGTCATC | TTACTGGCTA | TCGTGGCCTT | GTACGTCCGA | 780 |
| ATCTACTTCG | TAGTCCGCTC | AAGCCATGCG | GACGTTGCTG | GTCCTCAGAC | GCTGGCCCTG | 840 |
| CTCAAGACAG | TCACCATCGT | ACTGGGTGTT | TTCATCATCT | GCTGGCTGCC | GGCTTTTAGC | 900 |
| ATCCTTCTCT | TAGACTCTAC | CTGTCCCGTC | CGGGCCTGTC | CTGTCCTCTA | CAAAGCCCAT | 960 |
| TATTTCTTTG | CCTTCGCCAC | CCTCAACTCT | CTGCTCAACC | CTGTCATCTA | TACATGGCGT | 1020 |
| AGCCGGGACC | TTCGGAGGGA | GGTACTGAGG | CCCCTGCTGT | GCTGGCGGCA | GGGGAAGGGA | 1080 |
| GCAACAGGGC | GCAGAGGTGG | GAACCCTGGT | CACCGACTCC | TGCCCCTCCG | CAGCTCCAGC | 1140 |
| TCCCTGGAGA | GAGGCTTGCA | TATGCCTACA | TCGCCAACAT | TTCTGGAGGG | CAACACAGTG | 1200 |
| GTCTGAGGGG | AAATGTGAAC | TGATCTGTAA | CCAAGCCACA | GAGAGAGCTC | TGTGGGGAGA | 1260 |
| GACCAGGTGA | CCTCATCATG | TCCCTCAGTG | CCACAGGTCT | GGAGGAACTG | ACCACGGCTC | 1320 |
| ATAGGTCAGG | TGGCCAACGG | AGGCACTGAC | TAATCAGATT | GTAGTACTGT | GACTGTGGGG | 1380 |
| ACCATTAAGG | GTCTAGGGGG | ACAGCAGGCT | CGAGTTTAGG | GCTAGACATT | TGCCACTTGG | 1440 |
| TACATAGGGT | GTCGGCATCC | TGTCTGTCCT | ATCTTCCAGC | TTCCCGGTTC | CCTTCCTGCC | 1500 |
| TCCTCCTTTT | AAGGGCCTCT | CTACATAGCC | CCGGCTGGCT | AGAGCTTGCT | GTGCAGACCA | 1560 |
| GGCTGACCTG | GACCTCCCAG | AGATAGATCA | ACTAACTGTG | TCCTGAGTGC | TGGGATTTTA | 1620 |
| AAGCCGTGTG | CCCCCACACC | CGGCTCCTGC | CACCTTCCAG | AAGCAATCTT | AGGCCACTTG | 1680 |
| TTGAGGAAAC | ACTCTCCCCA | GAGGACCCAA | GCCTTCTTCC | CTGTCTCTCT | GAGGCCTGAA | 1740 |
| TCCACAGCTT | CCCCATTTTA | TCAACTGCTG | CTTCTTCCCT | TTCCTTCTGT | GTTCAGGGA | 1800 |
| AACCACTGTG | GGGCAGGGA | GGGGTCCTGG | GATCCCAGTT | TTTATGCTCA | GATCTCACTG | 1860 |
| AGCACTTGCT | TTATTGGGGA | GCAGAGAGGA | ATCAGCTGAG | GCAGTGTGGG | GCAGATGTTG | 1920 |
| AGGAGAATTT | GGGCTTCCTG | GTGAGAAAAC | TCTAGGGGAG | GCGTTGGTTA | TTCCTGGAAC | 1980 |
| CCAGCCTCTC | TCCCCACGAA | CTCTTCACAC | CCGCAGCCTT | GAGCTGGATG | CAAAGGCTGC | 2040 |
| TTTCAATTTG | TCTTTGTAGT | TTTGTTTTGT | TTGTTTTGT | TTTTTAAAT | TGGGACAGGA | 2100 |

|  |  |  |  |  |  |
|---|---|---|---|---|---|
| TCTCACGTAC | CCCAGGCTGG | CCTCCGACTC | ACTATGTAGC | CAAGGCTGGC | TTTGGACTTC | 2160 |
| TGACCCTCCT | GCCTCCGCTT | CTGGAGTGCA | GGTATTACAA | GGGTGTACCA | CCACCACCAC | 2220 |
| CACCACCAAC | AACAACAACA | ACAACAACAC | CTGTCTTGAA | AACTATCATG | AATGACATGG | 2280 |
| TTCACATAGC | CTTGGGTGGC | CAAGGACATC | CCGGATACTC | TTATGGCATC | TTCCTTGAAG | 2340 |
| GACTTTGCTA | AATCCTGTGG | AGAAGTAGAA | AATCCAATAC | GGTACAAACG | GTATTTATGT | 2400 |
| GTGTCTGTGT | ATCAGTGTGG | GGTCTGTGAC | CTCCTATCCC | AGTGTGGGTG | CTGTCTGACC | 2460 |
| TCTTATGTGC | ACATCCGTGT | CAAGACTGCT | AGAGAGATGG | ACGGGGTGT | GTGTGCTTGT | 2520 |
| GGGGGTCTAG | CCATGATCAG | GCCTCCTGGG | AATTGCTGAA | TCATCTCTCC | CACACACAGA | 2580 |
| CACACACCTC | CGCCTTAAAG | AAATGTGTGA | AAGAAAGGC | TGAGGAAGGG | GAGATTTGGG | 2640 |
| AGGCAAGGAG | CCAGTCGGGA | GTGTGTCTCC | CCTCATACAG | CTTCCCAGAT | GTCCCCCTTG | 2700 |
| TGCTGGAAAC | CCAGAACTGG | GCCAATAAAC | AGTTCAATTT | CTCTTGAAAA | AAAA | 2754 |

( 2 ) INFORMATION FOR SEQ ID NO:2:

( i ) SEQUENCE CHARACTERISTICS:
        ( A ) LENGTH: 352 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Gly Gly Leu Tyr Ser Glu Tyr Leu Asn Pro Glu Lys Val Gln Glu
 1               5                  10                  15

His Tyr Asn Tyr Thr Lys Glu Thr Leu Asp Met Gln Glu Thr Pro Ser
                20                  25                  30

Arg Lys Val Ala Ser Ala Phe Ile Ile Ile Leu Cys Cys Ala Ile Val
            35                  40                  45

Val Glu Asn Leu Leu Val Leu Ile Ala Val Ala Arg Asn Ser Lys Phe
        50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Pro Val
                85                  90                  95

Thr Leu Ser Leu Thr Pro Leu Gln Trp Phe Ala Arg Glu Gly Ser Ala
            100                 105                 110

Phe Ile Thr Leu Ser Ala Ser Val Phe Ser Leu Leu Ala Ile Ala Ile
        115                 120                 125

Glu Arg Gln Val Ala Ile Ala Lys Val Lys Leu Tyr Gly Ser Asp Lys
    130                 135                 140

Ser Cys Arg Met Leu Met Leu Ile Gly Ala Ser Trp Leu Ile Ser Leu
145                 150                 155                 160

Ile Leu Gly Gly Leu Pro Ile Leu Gly Trp Asn Cys Leu Asp His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Val Ile Leu Ala Ile Val Ala Leu
                195                 200                 205

Tyr Val Arg Ile Tyr Phe Val Val Arg Ser Ser His Ala Asp Val Ala
    210                 215                 220

Gly Pro Gln Thr Leu Ala Leu Leu Lys Thr Val Thr Ile Val Leu Gly
225                 230                 235                 240
```

5,585,476

-continued

| | | | | | | | | | | | | | | |
|---|---|---|---|---|---|---|---|---|---|---|---|---|---|---|
|Val|Phe|Ile|Ile|Cys|Trp|Leu|Pro|Ala|Phe|Ser|Ile|Leu|Leu|Leu|Asp
| | | |245| | | | |250| | | |255| |
|Ser|Thr|Cys|Pro|Val|Arg|Ala|Cys|Pro|Val|Leu|Tyr|Lys|Ala|His|Tyr
| | |260| | | | |265| | | |270| | |
|Phe|Phe|Ala|Phe|Ala|Thr|Leu|Asn|Ser|Leu|Leu|Asn|Pro|Val|Ile|Tyr
| |275| | | | |280| | | |285| | | |
|Thr|Trp|Arg|Ser|Arg|Asp|Leu|Arg|Arg|Glu|Val|Leu|Arg|Pro|Leu|Leu
|290| | | | |295| | | | |300| | | | |
|Cys|Trp|Arg|Gln|Gly|Lys|Gly|Ala|Thr|Gly|Arg|Arg|Gly|Gly|Asn|Pro
|305| | | |310| | | |315| | | | |320| |
|Gly|His|Arg|Leu|Leu|Pro|Leu|Arg|Ser|Ser|Ser|Ser|Leu|Glu|Arg|Gly
| | | |325| | | |330| | | |335| | | |
|Leu|His|Met|Pro|Thr|Ser|Pro|Thr|Phe|Leu|Glu|Gly|Asn|Thr|Val|Val
| | |340| | | |345| | | |350| | | | |

( 2 ) INFORMATION FOR SEQ ID NO:3:

( i ) SEQUENCE CHARACTERISTICS:
        ( A ) LENGTH: 2232 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 269..1420

( x i ) SEQUENCE DESCRIPTION: SEQ ID NO:3:

GAATTCTTTG CTGGTCTCCG TCAGTCGCCG ACAGCAGCAA GATGCGGATC GCGCGGTGTA    60

GACCCGGAGC CCGGCGGACG CAGCTTCGTC CCGCTTGAGC GAGGCTGCTG TTTCTCGGAG   120

GCCTCTCCAG CCAAGGAAAA ACTACATAAA AAAGCATCGG ATTGCTTGCT GACCTGGCCT   180

TGCTGTAACT GAAGGCTCGC TCAACCTCGC CCTCTAGCGT TTGTCTGGAG AAGTACCACC   240

CCGGGCTCCT GGGGACACAG TTGCGGCT ATG GTG TCC TCC ACC AGC ATC CCA   292
                                                           Met Val Ser Ser Thr Ser Ile Pro
                                                            1                  5

GTG GTT AAG GCT CTC CGC AGC CAA GTC TCC GAC TAT GGC AAC TAT GAT   340
Val Val Lys Ala Leu Arg Ser Gln Val Ser Asp Tyr Gly Asn Tyr Asp
    10                         15                       20

ATC ATA GTC CGG CAT TAC AAC TAC ACA GGC AAG CTG AAC ATC GGA GTG   388
Ile Ile Val Arg His Tyr Asn Tyr Thr Gly Lys Leu Asn Ile Gly Val
 25                        30                       35                       40

GAG AAG GAC CAT GGC ATT AAA CTG ACT TCA GTG GTG TTC ATT CTC ATC   436
Glu Lys Asp His Gly Ile Lys Leu Thr Ser Val Val Phe Ile Leu Ile
                      45                               50                       55

TGC TGC TTG ATC ATC CTA GAG AAT ATA TTT GTC TTG CTA ACT ATT TGG   484
Cys Cys Leu Ile Ile Leu Glu Asn Ile Phe Val Leu Leu Thr Ile Trp
                  60                             65                       70

AAA ACC AAG AAG TTC CAC CGG CCC ATG TAC TAT TTC ATA GGC AAC CTA   532
Lys Thr Lys Lys Phe His Arg Pro Met Tyr Tyr Phe Ile Gly Asn Leu
                75                       80                       85

GCC CTC TCG GAC CTG TTA GCA GGA GTG GCT TAC ACA GCT AAC CTG CTG   580
Ala Leu Ser Asp Leu Leu Ala Gly Val Ala Tyr Thr Ala Asn Leu Leu
 90                        95                              100

TTG TCT GGG GCC ACC ACC TAC AAG CTC ACA CCT GCC CAG TGG TTT CTG   628
Leu Ser Gly Ala Thr Thr Tyr Lys Leu Thr Pro Ala Gln Trp Phe Leu
105                    110                       115                       120

CGG GAA GGA AGT ATG TTT GTG GCT CTG TCT GCC TCA GTC TTC AGC CTC   676
Arg Glu Gly Ser Met Phe Val Ala Leu Ser Ala Ser Val Phe Ser Leu

```
                         125                          130                          135
CTT GCT ATC GCC ATT GAG CGC TAC ATC ACC ATG CTG AAG ATG AAA CTA             724
Leu Ala Ile Ala Ile Glu Arg Tyr Ile Thr Met Leu Lys Met Lys Leu
            140                 145                      150

CAC AAC GGC AGC AAC AGC TCG CGC TCC TTT CTG CTG ATC AGT GCC TGC             772
His Asn Gly Ser Asn Ser Ser Arg Ser Phe Leu Leu Ile Ser Ala Cys
            155                 160                      165

TGG GTC ATC TCC CTC ATC CTG GGT GGG CTG CCC ATC ATG GGC TGG AAC             820
Trp Val Ile Ser Leu Ile Leu Gly Gly Leu Pro Ile Met Gly Trp Asn
        170                 175                      180

TGC ATC AGC TCG CTG TCC AGC TGC TCC ACC GTG CTC CCG CTC TAC CAC             868
Cys Ile Ser Ser Leu Ser Ser Cys Ser Thr Val Leu Pro Leu Tyr His
185                 190                      195                      200

AAG CAC TAT ATT CTC TTC TGC ACC ACC GTC TTC ACC CTG CTC CTG CTT             916
Lys His Tyr Ile Leu Phe Cys Thr Thr Val Phe Thr Leu Leu Leu Leu
                    205                      210                 215

TCC ATC GTC ATC CTC TAC TGC AGG ATC TAC TCC TTG GTG AGG ACT CGA             964
Ser Ile Val Ile Leu Tyr Cys Arg Ile Tyr Ser Leu Val Arg Thr Arg
                220                      225                 230

AGC CGC CGC CTG ACC TTC CGC AAG AAC ATC TCC AAG GCC AGC CGC AGT            1012
Ser Arg Arg Leu Thr Phe Arg Lys Asn Ile Ser Lys Ala Ser Arg Ser
            235                      240                 245

TCC GAG AAG TCT CTG GCC TTG CTG AAG ACA GTG ATC ATT GTC CTG AGT            1060
Ser Glu Lys Ser Leu Ala Leu Leu Lys Thr Val Ile Ile Val Leu Ser
250                      255                 260

GTC TTC ATT GCC TGC TGG GCC CCT CTC TTC ATC CTA CTA CTT TTA GAT            1108
Val Phe Ile Ala Cys Trp Ala Pro Leu Phe Ile Leu Leu Leu Leu Asp
265                 270                 275                      280

GTG GGG TGC AAG GCG AAG ACC TGT GAC ATC CTG TAC AAA GCA GAG TAC            1156
Val Gly Cys Lys Ala Lys Thr Cys Asp Ile Leu Tyr Lys Ala Glu Tyr
                285                 290                      295

TTC CTG GTT CTG GCT GTG CTG AAC TCA GGT ACC AAC CCC ATC ATC TAC            1204
Phe Leu Val Leu Ala Val Leu Asn Ser Gly Thr Asn Pro Ile Ile Tyr
            300                 305                      310

ACT CTG ACC AAT AAG GAG ATG CGC CGG GCC TTC ATC AGG ATC ATA TCT            1252
Thr Leu Thr Asn Lys Glu Met Arg Arg Ala Phe Ile Arg Ile Ile Ser
        315                 320                      325

TGT TGC AAA TGC CCC AAC GGA GAC TCC GCT GGC AAA TTC AAG AGG CCC            1300
Cys Cys Lys Cys Pro Asn Gly Asp Ser Ala Gly Lys Phe Lys Arg Pro
330                 335                      340

ATC ATC CCG GGC ATG GAA TTT AGC CGC AGC AAA TCA GAC AAC TCC TCC            1348
Ile Ile Pro Gly Met Glu Phe Ser Arg Ser Lys Ser Asp Asn Ser Ser
345                 350                 355                      360

CAC CCC CAG AAG GAT GAT GGG GAC AAT CCA GAG ACC ATT ATG TCT TCT            1396
His Pro Gln Lys Asp Asp Gly Asp Asn Pro Glu Thr Ile Met Ser Ser
                365                 370                      375

GGA AAC GTC AAT TCT TCT TCT TAAAACCGGA AGCTGTTGAT ACTGTTGATT               1447
Gly Asn Val Asn Ser Ser Ser
            380

CTGGCTTCAT CACTCACTAC CCTAGCATTT CAAAAACATC TCTCTTTCTC CACTGCTGCA          1507

AGGAAGAAGC AGCCGGGAGC CTGAGAGAGG GAGGGAAGGG AGAATGTGCG GCTTGGTGAT          1567

ACCATGTTGT AGGTAGGTTA TGATTATGAA CAATGCCCTG GGAAGGGTGG AGATCAGATC          1627

TGCCTGCAGA GGGTTTCCTG CCCCCTCCTA ATCTCTTCAC TTCCTTCAGT CGTTTCTGTT          1687

TATCCCCCAT ACTCTTTTTT CTTTTCTCCG TTTTTCTCAT TCCCCTTCTC TACCATCGCT          1747

TTCTTTTCTC TTTCTTTAAA ATTTAGGGGC AACAAAAGGA ATCCCACAAA TGGATATTGT          1807

GGAAAACATA GTGCTGAATG ACGGCAAAGA ATGGTGGTAA ATCAAAAGAT AAATTAACTT          1867
```

```
CATAAGACTG CTATTCTGAA ATGCAACAAT CTTGTACAGT CAGGACTGAT AAAATGGAGC    1927

AATCAGACAT TCAGATGCC  CGTCAATGTA AAATCACCTA CTTGAACATT GTATGCAATA    1987

CATTCACACA AAAAAGCAAA TACTGTAGCC TTATTTGAAC AATACTGAAC TCATAAATAC    2047

TCATGGTTTC ACTCTGTCCA GGCGCCTAAG GACTATGCTG CTGTAATACA GGAAAACACA    2107

GCGGATGCCT CCTCTATTAA AATGTCACTC AAGAAAGTC  TCTTGTAACG TAAAGGCAAA    2167

CACATGTAGC TACTGAGCTA TGACTGTCCT TGGTCACACT CTATGGGAAA AACACCGGAC    2227

TCCAC                                                                2232
```

(2) INFORMATION FOR SEQ ID NO:4:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Ser Ser Thr Ser Ile Pro Val Val Lys Ala Leu Arg Ser Gln
 1               5                  10                  15

Val Ser Asp Tyr Gly Asn Tyr Asp Ile Ile Val Arg His Tyr Asn Tyr
                20                  25                  30

Thr Gly Lys Leu Asn Ile Gly Val Glu Lys Asp His Gly Ile Lys Leu
            35                  40                  45

Thr Ser Val Val Phe Ile Leu Ile Cys Cys Leu Ile Ile Leu Glu Asn
        50                  55                  60

Ile Phe Val Leu Leu Thr Ile Trp Lys Thr Lys Lys Phe His Arg Pro
 65                  70                  75                  80

Met Tyr Tyr Phe Ile Gly Asn Leu Ala Leu Ser Asp Leu Leu Ala Gly
                85                  90                  95

Val Ala Tyr Thr Ala Asn Leu Leu Leu Ser Gly Ala Thr Thr Tyr Lys
               100                 105                 110

Leu Thr Pro Ala Gln Trp Phe Leu Arg Glu Gly Ser Met Phe Val Ala
            115                 120                 125

Leu Ser Ala Ser Val Phe Ser Leu Leu Ala Ile Ala Ile Glu Arg Tyr
        130                 135                 140

Ile Thr Met Leu Lys Met Lys Leu His Asn Gly Ser Asn Ser Ser Arg
145                 150                 155                 160

Ser Phe Leu Leu Ile Ser Ala Cys Trp Val Ile Ser Leu Ile Leu Gly
                165                 170                 175

Gly Leu Pro Ile Met Gly Trp Asn Cys Ile Ser Ser Leu Ser Ser Cys
            180                 185                 190

Ser Thr Val Leu Pro Leu Tyr His Lys His Tyr Ile Leu Phe Cys Thr
        195                 200                 205

Thr Val Phe Thr Leu Leu Leu Leu Ser Ile Val Ile Leu Tyr Cys Arg
    210                 215                 220

Ile Tyr Ser Leu Val Arg Thr Arg Ser Arg Arg Leu Thr Phe Arg Lys
225                 230                 235                 240

Asn Ile Ser Lys Ala Ser Arg Ser Ser Glu Lys Ser Leu Ala Leu Leu
                245                 250                 255

Lys Thr Val Ile Ile Val Leu Ser Val Phe Ile Ala Cys Trp Ala Pro
            260                 265                 270

Leu Phe Ile Leu Leu Leu Leu Asp Val Gly Cys Lys Ala Lys Thr Cys
        275                 280                 285
```

| | | | | | | | | | | | | | |
|---|---|---|---|---|---|---|---|---|---|---|---|---|---|
| Asp | Ile | Leu | Tyr | Lys | Ala | Glu | Tyr | Phe | Leu | Val | Leu | Ala | Val | Leu | Asn |
| | 290 | | | | 295 | | | | | 300 | | | | |
| Ser | Gly | Thr | Asn | Pro | Ile | Ile | Tyr | Thr | Leu | Thr | Asn | Lys | Glu | Met | Arg |
| 305 | | | | | 310 | | | | | 315 | | | | | 320 |
| Arg | Ala | Phe | Ile | Arg | Ile | Ile | Ser | Cys | Cys | Lys | Cys | Pro | Asn | Gly | Asp |
| | | | | 325 | | | | | 330 | | | | | 335 |
| Ser | Ala | Gly | Lys | Phe | Lys | Arg | Pro | Ile | Ile | Pro | Gly | Met | Glu | Phe | Ser |
| | | | 340 | | | | | 345 | | | | | 350 | |
| Arg | Ser | Lys | Ser | Asp | Asn | Ser | Ser | His | Pro | Gln | Lys | Asp | Asp | Gly | Asp |
| | | 355 | | | | | 360 | | | | | 365 | | | |
| Asn | Pro | Glu | Thr | Ile | Met | Ser | Ser | Gly | Asn | Val | Asn | Ser | Ser | Ser | |
| | 370 | | | | | 375 | | | | | 380 | | | | |

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

| Lys | Glu | Thr | Leu | Asp | Met | Gln | Glu | Thr | Pro | Ser | Arg |
|---|---|---|---|---|---|---|---|---|---|---|---|
| 1 | | | | 5 | | | | | 10 | | |

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

| Tyr | Ser | Glu | Tyr | Leu | Asn | Pro | Glu | Lys | Val | Gln | Glu |
|---|---|---|---|---|---|---|---|---|---|---|---|
| 1 | | | | 5 | | | | | 10 | | |

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

| Arg | Gln | Gly | Lys | Gly | Ala | Thr | Gly | Arg | Arg | Gly | Gly |
|---|---|---|---|---|---|---|---|---|---|---|---|
| 1 | | | | 5 | | | | | 10 | | |

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

| Arg | Ser | Ser | Ser | Ser | Leu | Glu | Arg | Gly | Leu | His | Met |
|---|---|---|---|---|---|---|---|---|---|---|---|
| 1 | | | | 5 | | | | | 10 | | |

( 2 ) INFORMATION FOR SEQ ID NO:9:

(i) SEQUENCE CHARACTERISTICS:
  (A) LENGTH: 303 amino acids
  (B) TYPE: amino acid
  (C) STRANDEDNESS: Not Relevant
  (D) TOPOLOGY: Not Relevant (ii) MOLECULE TYPE: protein (xi) SEQUENCE DESCRIPTION: SEQ ID NO:9:

| Met 1 | Asp | Pro | Leu | Asn 5 | Leu | Ser | Trp | Tyr | Asp 10 | Asp | Leu | Glu | Arg | Gln 15 |
|---|---|---|---|---|---|---|---|---|---|---|---|---|---|---|
| Asn | Trp | Ser | Arg 20 | Pro | Phe | Asn | Gly | Ser 25 | Glu | Gly | Lys | Ala | Asp 30 | Arg | Pro |
| His | Tyr | Asn 35 | Tyr | Tyr | Ala | Met | Leu 40 | Leu | Thr | Leu | Leu | Ile 45 | Phe | Ile | Ile |
| Val | Phe 50 | Gly | Asn | Val | Leu | Val 55 | Cys | Met | Ala | Val | Ser 60 | Arg | Glu | Lys | Ala |
| Leu 65 | Gln | Thr | Thr | Thr | Asn 70 | Tyr | Leu | Ile | Val | Ser 75 | Leu | Ala | Val | Ala | Asp 80 |
| Leu | Leu | Val | Ala | Thr 85 | Leu | Val | Met | Pro | Trp 90 | Val | Val | Tyr | Leu | Glu 95 | Val |
| Val | Gly | Glu | Trp 100 | Lys | Phe | Ser | Arg | Ile 105 | His | Cys | Asp | Ile | Phe 110 | Val | Thr |
| Leu | Asp | Val 115 | Met | Met | Cys | Thr | Ala 120 | Ser | Ile | Leu | Asn | Leu 125 | Cys | Ala | Ile |
| Ser | Ile 130 | Asp | Arg | Tyr | Thr | Ala 135 | Val | Ala | Met | Pro | Met 140 | Leu | Tyr | Asn | Thr |
| Arg 145 | Tyr | Ser | Ser | Lys | Arg 150 | Arg | Val | Thr | Val | Met 155 | Ile | Ala | Ile | Val | Trp 160 |
| Val | Leu | Ser | Phe | Thr 165 | Ile | Ser | Cys | Pro | Leu 170 | Leu | Phe | Gly | Leu | Asn 175 | Asn |
| Thr | Asp | Gln | Asn 180 | Glu | Cys | Ile | Ile | Ala 185 | Asn | Pro | Ala | Phe | Val 190 | Val | Tyr |
| Ser | Ser | Ile 195 | Val | Ser | Phe | Tyr | Val 200 | Pro | Phe | Ile | Val | Thr 205 | Leu | Leu | Val |
| Tyr | Ile 210 | Lys | Ile | Tyr | Ile | Val 215 | Leu | Arg | Lys | Arg | Arg 220 | Lys | Arg | Val | Asn |
| Thr 225 | Lys | Lys | Glu | Lys | Lys 230 | Ala | Thr | Gln | Met | Leu 235 | Ala | Ile | Val | Leu | Gly 240 |
| Val | Phe | Ile | Ile | Cys 245 | Trp | Leu | Pro | Phe | Phe 250 | Ile | Thr | His | Ile | Leu 255 | Asn |
| Ile | His | Cys | Asp 260 | Cys | Asn | Ile | Pro | Pro 265 | Val | Leu | Tyr | Ser | Ala 270 | Phe | Thr |
| Trp | Leu | Gly 275 | Tyr | Val | Asn | Ser | Ala 280 | Val | Asn | Pro | Ile | Ile 285 | Tyr | Thr | Thr |
| Phe | Asn 290 | Ile | Glu | Phe | Arg | Lys 295 | Ala | Phe | Met | Lys | Ile 300 | Leu | His | Cys |

(2) INFORMATION FOR SEQ ID NO:10:

(i) SEQUENCE CHARACTERISTICS:
    (A) LENGTH: 377 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:10:

| | | | | | | | | | | | | | | |
|---|---|---|---|---|---|---|---|---|---|---|---|---|---|---|
| Met 1 | Gly | Pro | Pro | Gly 5 | Asn | Asp | Ser | Asp | Phe 10 | Leu | Leu | Thr | Thr | Asn 15 | Gly |
| Ser | His | Val | Pro 20 | Asp | His | Asp | Val | Thr 25 | Glu | Glu | Arg | Asp | Glu 30 | Ala | Trp |
| Val | Val | Gly 35 | Met | Ala | Ile | Leu | Met 40 | Ser | Val | Ile | Val | Leu 45 | Ala | Ile | Val |
| Phe | Gly 50 | Asn | Val | Leu | Val | Ile 55 | Thr | Ala | Ile | Ala | Lys 60 | Phe | Glu | Arg | Leu |
| Gln 65 | Thr | Val | Thr | Asn | Tyr 70 | Phe | Ile | Thr | Ser | Leu 75 | Ala | Cys | Ala | Asp | Leu 80 |
| Val | Met | Gly | Leu | Ala 85 | Val | Val | Pro | Phe | Gly 90 | Ala | Ser | His | Ile | Leu 95 | Met |
| Lys | Met | Trp | Asn 100 | Phe | Gly | Asn | Phe | Trp 105 | Cys | Glu | Phe | Trp | Thr 110 | Ser | Ile |
| Asp | Val | Leu 115 | Cys | Val | Thr | Ala | Ser 120 | Ile | Glu | Thr | Leu | Cys 125 | Val | Ile | Ala |
| Val | Asp 130 | Arg | Tyr | Ile | Ala | Ile 135 | Thr | Ser | Pro | Phe | Lys 140 | Tyr | Gln | Ser | Leu |
| Leu 145 | Thr | Lys | Asn | Lys | Ala 150 | Arg | Met | Val | Ile | Leu 155 | Met | Val | Trp | Ile | Val 160 |
| Ser | Gly | Leu | Thr | Ser 165 | Phe | Leu | Pro | Ile | Gln 170 | Met | His | Trp | Tyr | Arg 175 | Ala |
| Thr | His | Gln | Lys 180 | Ala | Ile | Asp | Cys | Tyr 185 | His | Arg | Glu | Thr | Cys 190 | Cys | Asp |
| Phe | Phe | Thr 195 | Asn | Gln | Ala | Tyr | Ala 200 | Ile | Ala | Ser | Ser | Ile 205 | Val | Ser | Phe |
| Tyr | Val 210 | Pro | Leu | Val | Val | Met 215 | Val | Phe | Val | Tyr | Ser 220 | Arg | Val | Phe | Gln |
| Val 225 | Ala | Lys | Arg | Gln | Leu 230 | Gln | Lys | Xaa | Xaa | Xaa 235 | Xaa | Xaa | Xaa | Xaa | Xaa 240 |
| Xaa | Xaa | Xaa | Xaa | Xaa 245 | Xaa | Xaa | Xaa | Xaa | Xaa 250 | Xaa | Xaa | Xaa | Xaa | Xaa 255 | Xaa |
| Xaa | Xaa | Xaa | Xaa 260 | Xaa | Xaa | Xaa | Xaa | Xaa 265 | Lys | Glu | His | Lys | Ala 270 | Leu | Lys |
| Thr | Leu | Gly 275 | Ile | Ile | Met | Gly | Ile 280 | Phe | Thr | Leu | Cys | Trp 285 | Leu | Pro | Phe |
| Phe | Ile 290 | Val | Asn | Ile | Val | His 295 | Val | Ile | Gln | Asp | Asn 300 | Leu | Ile | Pro | Lys |
| Glu 305 | Val | Tyr | Ile | Leu | Leu 310 | Asn | Trp | Leu | Gly | Tyr 315 | Val | Asn | Ser | Ala | Phe 320 |
| Asn | Pro | Leu | Ile | Tyr 325 | Cys | Arg | Ser | Pro | Asp 330 | Phe | Arg | Ile | Ala | Phe 335 | Gln |
| Glu | Leu | Leu | Cys 340 | Xaa | Xaa | Xaa | Xaa | Xaa 345 | Xaa | Xaa | Xaa | Xaa | Xaa 350 | Xaa | Xaa |
| Xaa | Xaa | Xaa 355 | Xaa | Xaa | Xaa | Xaa | Xaa | Xaa | Xaa | Xaa | Xaa | Xaa | Xaa 365 | Xaa | Xaa |
| Xaa | Xaa | Xaa 370 | Xaa | Xaa | Xaa | Xaa | Xaa 375 | Xaa | | | | | | | |

(2) INFORMATION FOR SEQ ID NO:11:

(i) SEQUENCE CHARACTERISTICS:
    (A) LENGTH: 450 amino acids
    (B) TYPE: amino acid
    (C) STRANDEDNESS: Not Relevant ( D ) TOPOLOGY: Not Relevant ( i i ) MOLECULE TYPE: protein ( x i ) SEQUENCE DESCRIPTION: SEQ ID NO:11:

```
Met Gly Ser Leu Gln Pro Asp Ala Gly Asn Ala Ser Trp Asn Gly Thr
 1               5                  10                  15

Glu Ala Pro Gly Gly Ala Arg Ala Thr Pro Tyr Ser Leu Gln Val
             20              25              30

Thr Leu Thr Leu Val Cys Leu Ala Gly Leu Leu Met Leu Leu Thr Val
         35                  40                  45

Phe Gly Asn Val Leu Val Ile Ile Ala Val Phe Thr Ser Arg Ala Leu
     50                  55                  60

Lys Ala Pro Gln Asn Leu Phe Leu Val Ser Leu Ala Ser Ala Asp Ile
 65                  70                  75                  80

Leu Val Ala Thr Leu Val Ile Pro Phe Ser Leu Ala Asn Glu Val Met
             85                  90                  95

Gly Tyr Trp Tyr Phe Gly Lys Thr Trp Cys Glu Ile Tyr Leu Ala Leu
             100                 105                 110

Asp Val Leu Phe Cys Thr Ser Ser Ile Val His Leu Cys Ala Ile Ser
             115                 120                 125

Leu Asp Arg Tyr Trp Ser Ile Thr Gln Ala Ile Glu Tyr Asn Leu Lys
     130                 135                 140

Arg Thr Pro Arg Arg Ile Lys Ala Ile Ile Ile Thr Val Trp Val Ile
 145                 150                 155                 160

Ser Ala Val Ile Ser Phe Pro Pro Leu Ile Ser Ile Glu Lys Lys Gly
             165                 170                 175

Gly Gly Gly Gly Pro Gln Pro Ala Glu Pro Arg Cys Glu Ile Asn Asp
             180                 185                 190

Gln Lys Trp Tyr Val Ile Ser Ser Cys Ile Gly Ser Phe Phe Ala Pro
     195                 200                 205

Cys Leu Ile Met Ile Leu Val Tyr Val Arg Ile Tyr Gln Ile Ala Lys
     210                 215                 220

Arg Arg Thr Arg Val Xaa Xaa Xaa Xaa Xaa Xaa Xaa Xaa Xaa Xaa
 225             230                 235                 240

Xaa Xaa Xaa Xaa Xaa Xaa Xaa Xaa Xaa Xaa Xaa Xaa Xaa Xaa Xaa
             245                 250                 255

Xaa Xaa Xaa Xaa Xaa Xaa Xaa Xaa Xaa Xaa Xaa Xaa Xaa Xaa Xaa
             260                 265                 270

Xaa Xaa Xaa Xaa Xaa Xaa Xaa Xaa Xaa Xaa Xaa Xaa Xaa Xaa Xaa
             275                 280                 285

Xaa Xaa Xaa Xaa Xaa Xaa Xaa Xaa Xaa Xaa Xaa Xaa Xaa Xaa Xaa
     290                 295                 300

Xaa Xaa Xaa Xaa Xaa Xaa Xaa Xaa Xaa Xaa Xaa Xaa Xaa Xaa Xaa
 305                 310                 315                 320

Xaa Xaa Xaa Xaa Xaa Xaa Xaa Xaa Xaa Xaa Xaa Xaa Xaa Xaa Xaa
             325                 330                 335

Xaa Xaa Xaa Xaa Xaa Xaa Xaa Xaa Xaa Xaa Xaa Xaa Xaa Xaa Xaa
             340                 345                 350

Xaa Xaa Xaa Xaa Xaa Xaa Xaa Xaa Xaa Xaa Xaa Xaa Xaa Xaa Arg
         355                 360                 365

Glu Lys Arg Phe Thr Phe Val Leu Ala Val Val Ile Gly Val Phe Val
     370                 375                 380

Val Cys Trp Phe Pro Phe Phe Phe Thr Tyr Thr Leu Thr Ala Val Gly
 385                 390                 395                 400
```

| Cys | Ser | Val | Pro | Arg<br>405 | Thr | Leu | Phe | Lys | Phe<br>410 | Phe | Phe | Trp | Phe | Gly<br>415 | Tyr |
|---|---|---|---|---|---|---|---|---|---|---|---|---|---|---|---|
| Cys | Asn | Ser | Ser<br>420 | Leu | Asn | Pro | Val | Ile<br>425 | Tyr | Thr | Ile | Phe | Asn<br>430 | His | Asp |
| Phe | Arg | Arg<br>435 | Ala | Phe | Lys | Lys | Ile<br>440 | Leu | Cys | Xaa | Xaa | Xaa<br>445 | Xaa | Xaa | Xaa |
| Xaa | Xaa<br>450 | | | | | | | | | | | | | | |

(2) INFORMATION FOR SEQ ID NO:12:

(i) SEQUENCE CHARACTERISTICS:
        (A) LENGTH: 421 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:12:

| Met<br>1 | Asp | Val | Leu | Ser<br>5 | Pro | Gly | Gly | Asn | Asn<br>10 | Thr | Thr | Ser | Pro | Pro<br>15 | Ala |
|---|---|---|---|---|---|---|---|---|---|---|---|---|---|---|---|
| Pro | Phe | Glu | Thr<br>20 | Gly | Gly | Asn | Thr | Thr<br>25 | Gly | Ile | Ser | Asp | Val<br>30 | Thr | Val |
| Ser | Tyr | Gln<br>35 | Val | Ile | Thr | Ser | Leu<br>40 | Leu | Leu | Gly | Thr | Leu<br>45 | Ile | Phe | Cys |
| Ala | Val | Leu<br>50 | Gly | Asn | Ala | Cys<br>55 | Val | Val | Ala | Ala | Ile<br>60 | Ala | Leu | Glu | Arg |
| Ser<br>65 | Leu | Gln | Asn | Val | Ala<br>70 | Asn | Tyr | Leu | Ile | Gly<br>75 | Ser | Leu | Ala | Val | Thr<br>80 |
| Asp | Leu | Met | Val | Ser<br>85 | Val | Leu | Val | Leu | Pro<br>90 | Met | Ala | Ala | Leu | Tyr<br>95 | Gln |
| Val | Leu | Asn | Lys<br>100 | Trp | Thr | Leu | Gly | Gln<br>105 | Val | Thr | Cys | Asp | Leu<br>110 | Phe | Ile |
| Ala | Leu | Asp<br>115 | Val | Leu | Cys | Cys | Thr<br>120 | Ser | Ser | Ile | Leu | His<br>125 | Leu | Cys | Ala |
| Ile | Ala<br>130 | Leu | Asp | Arg | Tyr | Trp<br>135 | Ala | Ile | Thr | Asp | Pro<br>140 | Ile | Asp | Tyr | Val |
| Asn<br>145 | Lys | Arg | Thr | Pro | Arg<br>150 | Pro | Arg | Ala | Leu | Thr<br>155 | Ser | Leu | Thr | Trp | Leu<br>160 |
| Ile | Gly | Phe | Leu | Ile<br>165 | Ser | Ile | Pro | Pro | Met<br>170 | Leu | Gly | Trp | Arg | Thr<br>175 | Pro |
| Glu | Asp | Arg | Ser<br>180 | Asp | Pro | Asp | Ala | Cys<br>185 | Thr | Ile | Ser | Lys | Asp<br>190 | Met | Gly |
| Tyr | Thr | Ile<br>195 | Tyr | Ser | Thr | Phe | Gly<br>200 | Ala | Phe | Tyr | Ile | Pro<br>205 | Leu | Leu | Leu |
| Met | Leu<br>210 | Val | Leu | Tyr | Gly | Arg<br>215 | Ile | Phe | Arg | Ala | Ala<br>220 | Arg | Phe | Arg | Ile |
| Pro<br>225 | Lys | Xaa | Xaa | Xaa | Xaa<br>230 | Xaa | Xaa | Xaa | Xaa | Xaa<br>235 | Xaa | Xaa | Xaa | Xaa | Xaa<br>240 |
| Xaa | Xaa | Xaa | Xaa | Xaa<br>245 | Xaa | Xaa | Xaa | Xaa | Xaa<br>250 | Xaa | Xaa | Xaa | Xaa | Xaa<br>255 | Xaa |
| Xaa | Xaa | Xaa | Xaa | Xaa<br>260 | Xaa | Xaa | Xaa | Xaa | Xaa<br>265 | Xaa | Xaa | Xaa | Xaa | Xaa<br>270 | Xaa |
| Xaa | Xaa | Xaa<br>275 | Xaa | Xaa | Xaa | Xaa | Xaa<br>280 | Xaa | Xaa | Xaa | Xaa | Xaa<br>285 | Xaa | Xaa | Xaa |

```
Xaa  Xaa  Xaa  Xaa  Xaa  Xaa  Xaa  Xaa  Xaa  Xaa  Xaa  Xaa  Xaa  Xaa  Xaa
     290                 295                 300

Xaa  Xaa  Xaa  Xaa  Xaa  Xaa  Xaa  Xaa  Xaa  Xaa  Xaa  Xaa  Xaa  Xaa  Xaa
305                      310                 315                      320

Xaa  Xaa  Xaa  Xaa  Xaa  Xaa  Xaa  Xaa  Xaa  Xaa  Xaa  Xaa  Xaa  Xaa  Xaa
                    325                      330                 335

Xaa  Arg  Glu  Arg  Lys  Thr  Val  Lys  Thr  Leu  Gly  Ile  Ile  Met  Gly  Thr
          340                      345                           350

Phe  Ile  Leu  Cys  Trp  Leu  Pro  Phe  Phe  Ile  Val  Ala  Leu  Val  Leu  Pro
          355                      360                      365

Phe  Cys  Glu  Ser  Ser  Cys  His  Met  Pro  Thr  Leu  Leu  Gly  Ala  Ile  Ile
     370                      375                      380

Asn  Trp  Leu  Gly  Tyr  Ser  Asn  Ser  Leu  Leu  Asn  Pro  Val  Ile  Tyr  Ala
385                      390                      395                           400

Tyr  Phe  Asn  Lys  Asp  Phe  Gln  Asn  Ala  Phe  Lys  Lys  Ile  Ile  Lys  Cys
               405                      410                           415

Xaa  Xaa  Xaa  Xaa  Xaa
               420
```

( 2 ) INFORMATION FOR SEQ ID NO:13:

( i ) SEQUENCE CHARACTERISTICS:
        ( A ) LENGTH: 461 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:13:

```
Met  Asn  Thr  Ser  Ala  Pro  Pro  Ala  Val  Ser  Pro  Asn  Ile  Thr  Val  Leu
1                   5                        10                           15

Ala  Pro  Gly  Lys  Gly  Pro  Trp  Gln  Val  Ala  Phe  Ile  Gly  Ile  Thr  Thr
               20                       25                           30

Gly  Leu  Leu  Ser  Leu  Ala  Thr  Val  Thr  Gly  Asn  Leu  Leu  Val  Ile  Ile
               35                       40                      45

Ser  Phe  Lys  Val  Asn  Thr  Glu  Leu  Lys  Thr  Val  Asn  Asn  Tyr  Phe  Leu
     50                       55                      60

Leu  Ser  Leu  Ala  Cys  Ala  Asp  Leu  Ile  Ile  Gly  Thr  Phe  Ser  Met  Asn
65                       70                      75                           80

Leu  Tyr  Thr  Thr  Tyr  Leu  Leu  Met  Gly  His  Trp  Ala  Leu  Gly  Thr  Leu
                    85                       90                           95

Ala  Cys  Asp  Leu  Trp  Leu  Ala  Leu  Asp  Tyr  Val  Ala  Ser  Asn  Ala  Ser
               100                      105                      110

Val  Met  Asn  Leu  Leu  Leu  Ile  Ser  Phe  Asp  Arg  Tyr  Phe  Ser  Val  Thr
          115                      120                      125

Arg  Pro  Leu  Ser  Tyr  Arg  Ala  Lys  Arg  Thr  Pro  Arg  Arg  Ala  Ala  Leu
     130                      135                      140

Met  Ile  Gly  Leu  Ala  Trp  Leu  Val  Ser  Phe  Val  Leu  Trp  Ala  Pro  Ala
145                      150                      155                           160

Ile  Leu  Phe  Trp  Gln  Tyr  Leu  Val  Gly  Glu  Arg  Thr  Val  Leu  Ala  Gly
                    165                      170                           175

Gln  Cys  Tyr  Ile  Gln  Phe  Leu  Ser  Gln  Pro  Ile  Ile  Thr  Phe  Gly  Thr
               180                      185                      190

Ala  Met  Ala  Ala  Phe  Tyr  Leu  Pro  Val  Thr  Val  Met  Cys  Thr  Leu  Tyr
          195                      200                      205

Trp  Arg  Ile  Tyr  Arg  Glu  Thr  Glu  Asn  Arg  Ala  Arg  Glu  Xaa  Xaa  Xaa
```

```
             210                    215                      220
Xaa  Xaa  Xaa  Xaa  Xaa  Xaa  Xaa  Xaa  Xaa  Xaa  Xaa  Xaa  Xaa  Xaa  Xaa
225                      230                      235                      240

Xaa  Xaa  Xaa  Xaa  Xaa  Xaa  Xaa  Xaa  Xaa  Xaa  Xaa  Xaa  Xaa  Xaa  Xaa
                    245                      250                      255

Xaa  Xaa  Xaa  Xaa  Xaa  Xaa  Xaa  Xaa  Xaa  Xaa  Xaa  Xaa  Xaa  Xaa  Xaa
               260                      265                      270

Xaa  Xaa  Xaa  Xaa  Xaa  Xaa  Xaa  Xaa  Xaa  Xaa  Xaa  Xaa  Xaa  Xaa  Xaa
          275                      280                      285

Xaa  Xaa  Xaa  Xaa  Xaa  Xaa  Xaa  Xaa  Xaa  Xaa  Xaa  Xaa  Xaa  Xaa  Xaa
     290                      295                      300

Xaa  Xaa  Xaa  Xaa  Xaa  Xaa  Xaa  Xaa  Xaa  Xaa  Xaa  Xaa  Xaa  Xaa  Xaa
305                      310                      315                      320

Xaa  Xaa  Xaa  Xaa  Xaa  Xaa  Xaa  Xaa  Xaa  Xaa  Xaa  Xaa  Xaa  Xaa  Xaa
                    325                      330                      335

Xaa  Xaa  Xaa  Xaa  Xaa  Xaa  Xaa  Xaa  Xaa  Xaa  Xaa  Xaa  Xaa  Xaa  Xaa
               340                      345                      350

Xaa  Xaa  Xaa  Xaa  Xaa  Xaa  Xaa  Lys  Glu  Lys  Lys  Ala  Ala  Arg  Thr  Leu
          355                      360                      365

Ser  Ala  Ile  Leu  Leu  Ala  Phe  Ile  Val  Thr  Trp  Thr  Pro  Tyr  Asn  Ile
     370                      375                      380

Met  Val  Leu  Val  Ser  Thr  Phe  Cys  Lys  Asp  Cys  Val  Pro  Glu  Thr  Leu
385                      390                      395                      400

Trp  Glu  Leu  Gly  Tyr  Trp  Leu  Cys  Tyr  Val  Asn  Ser  Thr  Ile  Asn  Pro
                    405                      410                      415

Met  Cys  Tyr  Ala  Leu  Cys  Asn  Lys  Ala  Phe  Arg  Asp  Thr  Phe  Arg  Leu
               420                      425                      430

Leu  Leu  Leu  Cys  Xaa  Xaa  Xaa  Xaa  Xaa  Xaa  Xaa  Xaa  Xaa  Xaa  Xaa
          435                      440                      445

Xaa  Xaa  Xaa  Xaa  Xaa  Xaa  Xaa  Xaa  Xaa  Xaa  Xaa  Xaa
     450                      455                      460
```

( 2 ) INFORMATION FOR SEQ ID NO:14:

( i ) SEQUENCE CHARACTERISTICS:
    ( A ) LENGTH: 387 amino acids
    ( B ) TYPE: amino acid
    ( C ) STRANDEDNESS: Not Relevant
    ( D ) TOPOLOGY: Not Relevant ( i i ) MOLECULE TYPE: protein ( x i ) SEQUENCE DESCRIPTION: SEQ ID NO:14:

```
Met  Gly  Ala  Cys  Val  Val  Met  Thr  Asp  Ile  Asn  Ile  Ser  Ser  Gly  Leu
1              5                        10                       15

Asp  Ser  Asn  Ala  Thr  Gly  Ile  Thr  Ala  Phe  Ser  Met  Pro  Gly  Trp  Gln
                    20                       25                       30

Leu  Ala  Leu  Trp  Thr  Ala  Ala  Tyr  Leu  Ala  Leu  Val  Leu  Val  Ala  Val
               35                       40                       45

Met  Gly  Asn  Ala  Thr  Val  Ile  Trp  Ile  Ile  Leu  Ala  His  Gln  Arg  Met
50                       55                       60

Arg  Thr  Val  Thr  Asn  Tyr  Phe  Ile  Val  Asn  Leu  Ala  Leu  Ala  Asp  Leu
65                       70                       75                       80

Cys  Met  Ala  Ala  Phe  Asn  Ala  Ala  Phe  Asn  Phe  Val  Tyr  Ala  Ser  His
                    85                       90                       95

Asn  Ile  Trp  Tyr  Phe  Gly  Arg  Ala  Phe  Cys  Tyr  Phe  Gln  Asn  Leu  Phe
               100                      105                      110
```

| Pro | Ile | Thr | Ala | Met | Phe | Val | Ser | Ile | Tyr | Ser | Met | Thr | Ala | Ile | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |
| Ala | Asp | Arg | Tyr | Met | Ala | Ile | Val | His | Pro | Phe | Gln | Pro | Arg | Leu | Ser |
|     | 130 |     |     |     |     | 135 |     |     |     |     | 140 |     |     |     |     |
| Ala | Pro | Gly | Thr | Arg | Ala | Val | Ile | Ala | Gly | Ile | Trp | Leu | Val | Ala | Leu |
| 145 |     |     |     |     | 150 |     |     |     |     | 155 |     |     |     |     | 160 |
| Ala | Leu | Ala | Phe | Pro | Gln | Cys | Phe | Tyr | Ser | Thr | Ile | Thr | Thr | Asp | Glu |
|     |     |     |     | 165 |     |     |     |     | 170 |     |     |     |     | 175 |     |
| Gly | Ala | Thr | Lys | Cys | Val | Val | Ala | Trp | Pro | Glu | Asp | Ser | Gly | Gly | Lys |
|     |     |     | 180 |     |     |     |     | 185 |     |     |     |     | 190 |     |     |
| Met | Leu | Leu | Leu | Tyr | His | Leu | Ile | Val | Ile | Ala | Leu | Ile | Tyr | Phe | Leu |
|     |     | 195 |     |     |     |     | 200 |     |     |     |     | 205 |     |     |     |
| Pro | Leu | Val | Val | Met | Phe | Val | Ala | Tyr | Ser | Val | Ile | Gly | Leu | Thr | Leu |
|     | 210 |     |     |     |     | 215 |     |     |     |     | 220 |     |     |     |     |
| Trp | Arg | Arg | Ser | Val | Pro | Xaa | Xaa | Xaa | Xaa | Xaa | Xaa | Xaa | Xaa | Xaa | Xaa |
| 225 |     |     |     |     | 230 |     |     |     |     | 235 |     |     |     |     | 240 |
| Xaa | Xaa | Xaa | Ala | Lys | Lys | Lys | Phe | Val | Lys | Thr | Met | Val | Leu | Val | Val |
|     |     |     |     | 245 |     |     |     |     | 250 |     |     |     |     | 255 |     |
| Val | Thr | Phe | Ala | Ile | Cys | Trp | Leu | Pro | Tyr | His | Leu | Tyr | Phe | Ile | Leu |
|     |     |     | 260 |     |     |     |     | 265 |     |     |     |     | 270 |     |     |
| Gly | Thr | Phe | Gln | Glu | Asp | Ile | Tyr | Cys | His | Lys | Phe | Ile | Gln | Gln | Val |
|     |     | 275 |     |     |     |     | 280 |     |     |     |     | 285 |     |     |     |
| Tyr | Leu | Ala | Leu | Phe | Trp | Leu | Ala | Met | Ser | Ser | Thr | Met | Tyr | Asn | Pro |
|     | 290 |     |     |     |     | 295 |     |     |     |     | 300 |     |     |     |     |
| Ile | Ile | Tyr | Cys | Cys | Leu | Asn | His | Arg | Phe | Arg | Ser | Gly | Phe | Arg | Leu |
| 305 |     |     |     |     | 310 |     |     |     |     | 315 |     |     |     |     | 320 |
| Ala | Phe | Arg | Cys | Xaa | Xaa | Xaa | Xaa | Xaa | Xaa | Xaa | Xaa | Xaa | Xaa | Xaa | Xaa |
|     |     |     |     | 325 |     |     |     |     | 330 |     |     |     |     | 335 |     |
| Xaa | Xaa | Xaa | Xaa | Xaa | Xaa | Xaa | Xaa | Xaa | Xaa | Xaa | Xaa | Xaa | Xaa | Xaa | Xaa |
|     |     |     | 340 |     |     |     |     | 345 |     |     |     |     | 350 |     |     |
| Xaa | Xaa | Xaa | Xaa | Xaa | Xaa | Xaa | Xaa | Xaa | Xaa | Xaa | Xaa | Xaa | Xaa | Xaa | Xaa |
|     |     | 355 |     |     |     |     | 360 |     |     |     |     | 365 |     |     |     |
| Xaa | Xaa | Xaa | Xaa | Xaa | Xaa | Xaa | Xaa | Xaa | Xaa | Xaa | Xaa | Xaa | Xaa | Xaa | Xaa |
|     | 370 |     |     |     |     | 375 |     |     |     |     | 380 |     |     |     |     |
| Xaa | Xaa | Xaa |     |     |     |     |     |     |     |     |     |     |     |     |     |
| 385 |     |     |     |     |     |     |     |     |     |     |     |     |     |     |     |